(12) United States Patent
Kannangara et al.

(10) Patent No.: US 10,724,012 B2
(45) Date of Patent: *Jul. 28, 2020

(54) GLYCOSYLTRANSFERASE GLYCOSYLATING FLAVOKERMESIC ACID AND/OR KERMESIC ACID

(71) Applicants: Københavns Universitet, København N (DK); Danmarks Tekniske Universitet, Lyngby (DK)

(72) Inventors: Rubini Maya Kannangara, Frederiksberg (DK); Mads Bennedsen, Græsted (DK); Bjørn Madsen, Helsingør (DK); Kim Binderup, Charlottelund (DK); Ulf Thrane, Helsinge (DK); Rasmus John Normand Frandsen, Allerød (DK); Uffe Hasbro Mortensen, Copenhagen N (DK); Birger Lindberg Møller, Brønshøj (DK); Finn Thyge Okkels, Roskilde (DK)

(73) Assignees: Københavns Universitet, København N (DK); Danmarks Tekniske Universitet, Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/160,396

(22) Filed: Oct. 15, 2018

(65) Prior Publication Data

US 2019/0048328 A1 Feb. 14, 2019

Related U.S. Application Data

(63) Continuation of application No. 15/105,673, filed as application No. PCT/EP2014/078540 on Dec. 18, 2014, now Pat. No. 10,100,290.

(30) Foreign Application Priority Data

Dec. 18, 2013 (EP) ..................................... 13198110

(51) Int. Cl.
| | | |
|---|---|---|
| *C12P 7/66* | (2006.01) | |
| *C12N 9/10* | (2006.01) | |
| *C12N 15/81* | (2006.01) | |
| *C12N 15/63* | (2006.01) | |
| *C12N 1/14* | (2006.01) | |

(Continued)

(52) U.S. Cl.
CPC ............. *C12N 9/1048* (2013.01); *C12N 1/14* (2013.01); *C12N 1/20* (2013.01); *C12N 9/1051* (2013.01);

(Continued)

(58) Field of Classification Search
None
See application file for complete search history.

(56) References Cited

U.S. PATENT DOCUMENTS 10,100,290 B2 * 10/2018 Kannangara ......... C12N 9/1048
2005/0277766 A1 12/2005 Wier et al.

(Continued)

FOREIGN PATENT DOCUMENTS

| CN | 103328630 A | 9/2013 |
|---|---|---|
| CN | 103352031 A | 10/2013 |

(Continued)

OTHER PUBLICATIONS

Chavez-Moreno C K et al: Metabolic profiling of Dactylopius (*Hemiptera dactylopiidae*) species pigments by geographical data analysis; Biochemical Systematics and Ecology, Pergamon Press, GB, Aug. 1, 2010, vol. 38, No. 4, pp. 671-679.

(Continued)

*Primary Examiner* — Richard C Ekstrom
(74) *Attorney, Agent, or Firm* — Woodard, Emhardt, Henry, Reeves & Wagner, LLP

(57) ABSTRACT

An isolated glycosyltransferase (GT) polypeptide capable of: (I): conjugating glucose to flavokermesic acid (FK); and/or (II): conjugating glucose to kermesic acid (KA) and use of this GT to e.g. make Carminic acid.

11 Claims, 9 Drawing Sheets

Figure 1:
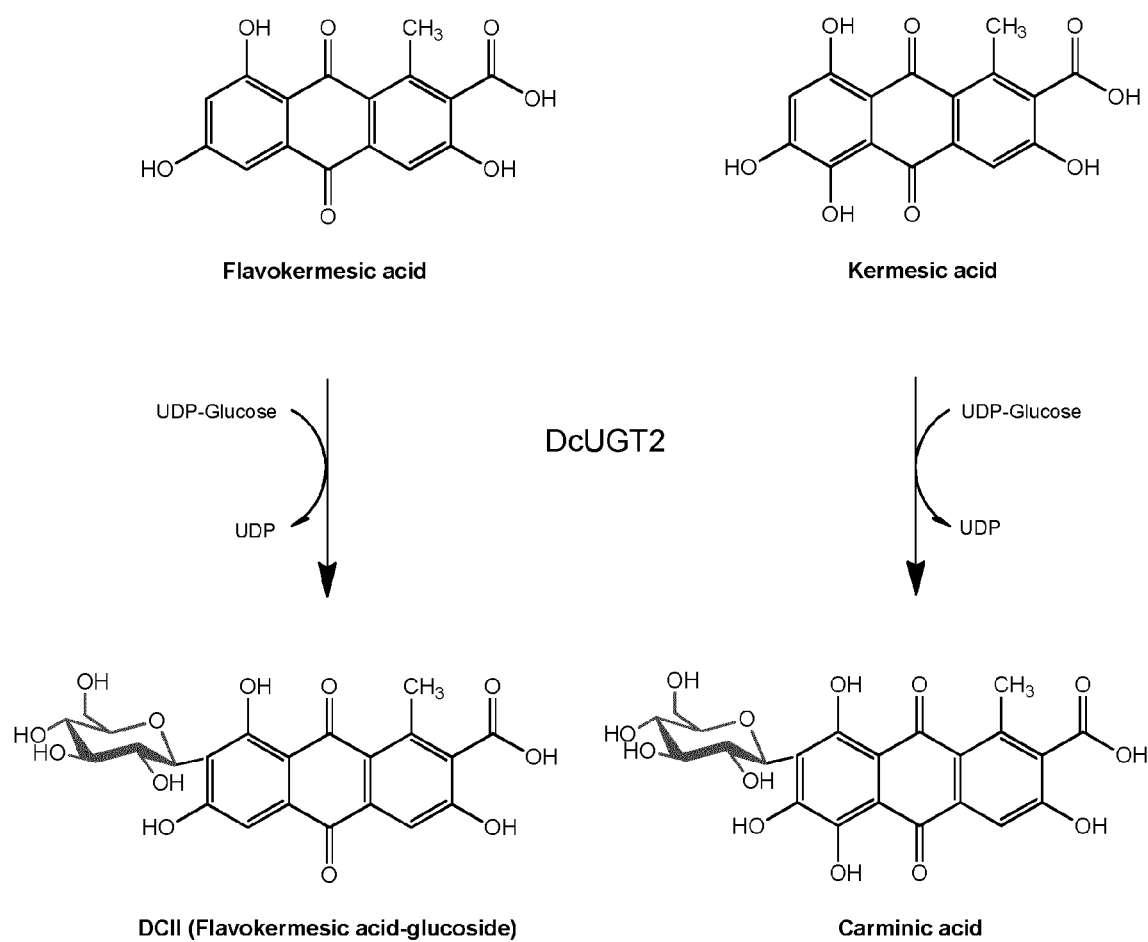

Specification includes a Sequence Listing.

(51) Int. Cl.
*C12N 15/80* (2006.01)
*C12N 1/20* (2006.01)

(52) U.S. Cl.
CPC .............. *C12N 15/63* (2013.01); *C12N 15/80* (2013.01); *C12N 15/81* (2013.01); *C12N 15/815* (2013.01); *C12P 7/66* (2013.01); *C12Y 204/00* (2013.01)

(56) References Cited

U.S. PATENT DOCUMENTS

2011/0318793 A1* 12/2011 Hansen ................ C12N 9/1051
435/128
2015/0232889 A1    8/2015 Hansen et al.
2015/0267227 A1    9/2015 Lindberg Moller et al.
2016/0376569 A1   12/2016 Kannangara et al.

FOREIGN PATENT DOCUMENTS

WO    WO 1992/01664 A1    2/1992
WO    WO 2012/097950 A1   7/2012
WO    WO 2016/198564 A1  12/2016

OTHER PUBLICATIONS

Guo et al., 'Protein tolerance to random amino acid change', Proc Natl Acad Sci U S A, Jun. 22, 2004; 101(25): 9205-9210. Published online Jun. 14, 2004. doi: 10.1073/pnas.0403255101PMCID: PMC438954 Biochemistry, [online] [retrieved from the Internet: <URL: https://www.ncbi.nlm.nih.gov/pmc/articles/PMC438954/>.

International Search Reported issued in related PCT/EP2014/078540 dated Mar. 19, 2015.

Irfan Baig et al, On the Acceptor Substrate of C-Glycosyltransferase UrdGT2: Three Prejamodmycin C-Glycosides from an Engineered Mutant of Streptomyces globisporus 1912 Delta-IndE (urdGT2), Angewandte Chemie International Edition Wiley-V C H Verlag GMBH & Co. KGAA, DE, Nov. 27, 2006, vol. 45, No. 46, pp. 7842-7846.

Robyn Meech et al.; The glycosidation of xenobiotics and endogenous compounds: Versatility and redundancy in the UDP glycosyltransferase superfamily, Pharmacology and Therapeutics, Feb. 2012, vol. 134, No. 2, pp. 200-218.

Stathopoulou et al., 'Structure elucidation and chromatographic identification of anthraquinone components of cochineal (*Dactylopius coccus*) detected in historical objects', Anal Chim Acta, Dec. 4, 2013;804:264-72. doi: 10.1016/j.aca.2013.09.053. Epub Oct. 5, 2013., [online] Dec. 2013 [retrieved on Oct. 6, 2017] Retrieved from the Internet: < URL: https://www.ncbi.nlm.nih.gov/pubmed/24267092>.

Written Opinion issued in related PCT/EP2014/078540 dated Mar. 19, 2015.

Velisek, J.et al., "Biosynthesis of Food Constituents: Natural Pigments. Part 1—a Review." Czech J. Food Sci. vol. 25, No. 6: 291-315. Aug. 3, 2007. 25 pages.

* cited by examiner

SEQUENCE LISTING

```
<160> NUMBER OF SEQ ID NOS: 5

<210> SEQ ID NO 1
<211> LENGTH: 1548
<212> TYPE: DNA
<213> ORGANISM: Dactylopius coccus costa
<220> FEATURE:
<221> NAME/KEY: CDS
<222> LOCATION: (1)..(1548)

<400> SEQUENCE: 1 atg gaa ttt cgt tta cta atc ctg gct ctt ttt tct gta ctt atg agt      48
Met Glu Phe Arg Leu Leu Ile Leu Ala Leu Phe Ser Val Leu Met Ser
1               5                   10                  15 act tca aac gga gca gaa att tta gct ctt ttc cct att cac ggt atc      96
Thr Ser Asn Gly Ala Glu Ile Leu Ala Leu Phe Pro Ile His Gly Ile
                20                  25                  30 agt aat tat aat gtt gct gaa gca ctg ctg aag acc tta gct aac cgg     144
Ser Asn Tyr Asn Val Ala Glu Ala Leu Leu Lys Thr Leu Ala Asn Arg
            35                  40                  45 ggt cat aat gtt aca gtt gtc aca tct ttt cct caa aaa aaa cct gta     192
Gly His Asn Val Thr Val Val Thr Ser Phe Pro Gln Lys Lys Pro Val
        50                  55                  60 cct aat ttg tac gaa att gac gta tct gga gct aaa ggc ttg gct act     240
Pro Asn Leu Tyr Glu Ile Asp Val Ser Gly Ala Lys Gly Leu Ala Thr
65                  70                  75                  80 aat tca ata cat ttt gaa aga tta caa acg att att caa gat gta aaa     288
Asn Ser Ile His Phe Glu Arg Leu Gln Thr Ile Ile Gln Asp Val Lys
                85                  90                  95 tcg aac ttt aag aac atg gta cga ctt agc aga aca tac tgt gag att     336
Ser Asn Phe Lys Asn Met Val Arg Leu Ser Arg Thr Tyr Cys Glu Ile
                100                 105                 110 atg ttt tct gat ccg agg gtt ttg aac att cga gac aag aaa ttc gat     384
Met Phe Ser Asp Pro Arg Val Leu Asn Ile Arg Asp Lys Lys Phe Asp
            115                 120                 125 ctc gta ata aac gcc gta ttt ggc agt gac tgc gat gcc gga ttc gca     432
Leu Val Ile Asn Ala Val Phe Gly Ser Asp Cys Asp Ala Gly Phe Ala
        130                 135                 140 tgg aaa agt caa gct cca ttg att tca att ctc aat gct aga cat act     480
Trp Lys Ser Gln Ala Pro Leu Ile Ser Ile Leu Asn Ala Arg His Thr
145                 150                 155                 160
```

```
cct tgg gcc cta cac aga atg gga aat cca tca aat cca gcg tat atg      528
Pro Trp Ala Leu His Arg Met Gly Asn Pro Ser Asn Pro Ala Tyr Met
            165                 170                 175 cct gtc att cat tct aga ttt cct gta aaa atg aat ttc ttc caa aga      576
Pro Val Ile His Ser Arg Phe Pro Val Lys Met Asn Phe Phe Gln Arg
            180                 185                 190 atg ata aat acg ggt tgg cat ttg tat ttt ctg tac atg tac ttt tat      624
Met Ile Asn Thr Gly Trp His Leu Tyr Phe Leu Tyr Met Tyr Phe Tyr
            195                 200                 205 tat ggt aat gga gaa gat gcc aac aaa atg gcg aga aaa ttt ttt ggc      672
Tyr Gly Asn Gly Glu Asp Ala Asn Lys Met Ala Arg Lys Phe Phe Gly
    210                 215                 220 aac gac atg ccc gac ata aat gaa atg gtt ttt aat aca tct tta tta      720
Asn Asp Met Pro Asp Ile Asn Glu Met Val Phe Asn Thr Ser Leu Leu
225                 230                 235                 240 ttc gta aat act cac ttt tcg gtt gat atg cca tat cct ttg gtt cca      768
Phe Val Asn Thr His Phe Ser Val Asp Met Pro Tyr Pro Leu Val Pro
            245                 250                 255 aac tgc att gaa ata gga gga ata cat gta aaa gag cca caa cca ctg      816
Asn Cys Ile Glu Ile Gly Gly Ile His Val Lys Glu Pro Gln Pro Leu
            260                 265                 270 cct ttg gaa ata caa aaa ttc atg gac gaa gca gaa cat ggg gtc att      864
Pro Leu Glu Ile Gln Lys Phe Met Asp Glu Ala Glu His Gly Val Ile
            275                 280                 285 ttc ttc acg cta gga tca atg gtg cgt act tcc acg ttt cca aat caa      912
Phe Phe Thr Leu Gly Ser Met Val Arg Thr Ser Thr Phe Pro Asn Gln
            290                 295                 300 act att caa gca ttt aag gaa gct ttt gcc gaa tta cct caa aga gtc      960
Thr Ile Gln Ala Phe Lys Glu Ala Phe Ala Glu Leu Pro Gln Arg Val
305                 310                 315                 320 tta tgg aag ttt gag aat gaa aat gag gat atg cca tca aat gta ctc     1008
Leu Trp Lys Phe Glu Asn Glu Asn Glu Asp Met Pro Ser Asn Val Leu
            325                 330                 335 ata agg aaa tgg ttt cca caa aat gat ata ttc ggt cat aag aat atc     1056
Ile Arg Lys Trp Phe Pro Gln Asn Asp Ile Phe Gly His Lys Asn Ile
            340                 345                 350 aaa gca ttc att agt cac ggt gga aat tct gga gct ctg gag gct gtt     1104
Lys Ala Phe Ile Ser His Gly Gly Asn Ser Gly Ala Leu Glu Ala Val
            355                 360                 365 cat ttc gga gta ccg ata att gga att cct tta ttc tac gat cag tac     1152
His Phe Gly Val Pro Ile Ile Gly Ile Pro Leu Phe Tyr Asp Gln Tyr
    370                 375                 380 agg aat att ttg agt ttc gtt aaa gaa ggt gtt gcc gtt ctt ttg gat     1200
Arg Asn Ile Leu Ser Phe Val Lys Glu Gly Val Ala Val Leu Leu Asp
385                 390                 395                 400 gtg aat gat ctg acg aaa gat aat att tta tct tct gtc agg act gtt     1248
Val Asn Asp Leu Thr Lys Asp Asn Ile Leu Ser Ser Val Arg Thr Val
            405                 410                 415 gtt aat gat aag agt tac tca gaa cgt atg aaa gca ttg tca caa cta     1296
Val Asn Asp Lys Ser Tyr Ser Glu Arg Met Lys Ala Leu Ser Gln Leu
            420                 425                 430 ttc cga gat cga cca atg agt cct ctt gac aca gct gtt tac tgg aca     1344
Phe Arg Asp Arg Pro Met Ser Pro Leu Asp Thr Ala Val Tyr Trp Thr
            435                 440                 445 gaa tat gtc atc cgc cat aga gga gcc cat cac ctc aag acc gct ggc     1392
Glu Tyr Val Ile Arg His Arg Gly Ala His His Leu Lys Thr Ala Gly
    450                 455                 460 gca ttt ttg cat tgg tat cag tat tta ctt ttt gac gtt att acc ttc     1440
Ala Phe Leu His Trp Tyr Gln Tyr Leu Leu Phe Asp Val Ile Thr Phe
```

|     |     |     |     |     |     |     |     |     |     |     |     |     |     |     |     |      |
|---|---|---|---|---|---|---|---|---|---|---|---|---|---|---|---|---|
|     | 465 |     |     |     | 470 |     |     |     | 475 |     |     |     | 480 |     |     |      |
| tta | tta | gtc | aca | ttc | tgc | gct | ttt | tgt | ttt | att | gtg | aaa | tat | ata | tgt | 1488 |
| Leu | Leu | Val | Thr | Phe | Cys | Ala | Phe | Cys | Phe | Ile | Val | Lys | Tyr | Ile | Cys |      |
|     |     |     |     | 485 |     |     |     |     | 490 |     |     |     |     | 495 |     |      |
| aaa | gct | ctc | att | cat | cat | tat | tgg | agc | agt | tcg | aaa | tct | gaa | aag | ttg | 1536 |
| Lys | Ala | Leu | Ile | His | His | Tyr | Trp | Ser | Ser | Ser | Lys | Ser | Glu | Lys | Leu |      |
|     |     |     | 500 |     |     |     |     | 505 |     |     |     |     | 510 |     |     |      |
| aaa | aaa | aat | taa |     |     |     |     |     |     |     |     |     |     |     |     | 1548 |
| Lys | Lys | Asn |     |     |     |     |     |     |     |     |     |     |     |     |     |      |
|     |     | 515 |     |     |     |     |     |     |     |     |     |     |     |     |     |      |

<210> SEQ ID NO 2
<211> LENGTH: 515
<212> TYPE: PRT
<213> ORGANISM: Dactylopius coccus costa

<400> SEQUENCE: 2

Met Glu Phe Arg Leu Leu Ile Leu Ala Leu Phe Ser Val Leu Met Ser
1               5                   10                  15

Thr Ser Asn Gly Ala Glu Ile Leu Ala Leu Phe Pro Ile His Gly Ile
            20                  25                  30

Ser Asn Tyr Asn Val Ala Glu Ala Leu Leu Lys Thr Leu Ala Asn Arg
        35                  40                  45

Gly His Asn Val Thr Val Val Thr Ser Phe Pro Gln Lys Lys Pro Val
    50                  55                  60

Pro Asn Leu Tyr Glu Ile Asp Val Ser Gly Ala Lys Gly Leu Ala Thr
65                  70                  75                  80

Asn Ser Ile His Phe Glu Arg Leu Gln Thr Ile Ile Gln Asp Val Lys
                85                  90                  95

Ser Asn Phe Lys Asn Met Val Arg Leu Ser Arg Thr Tyr Cys Glu Ile
            100                 105                 110

Met Phe Ser Asp Pro Arg Val Leu Asn Ile Arg Asp Lys Lys Phe Asp
        115                 120                 125

Leu Val Ile Asn Ala Val Phe Gly Ser Asp Cys Asp Ala Gly Phe Ala
    130                 135                 140

Trp Lys Ser Gln Ala Pro Leu Ile Ser Ile Leu Asn Ala Arg His Thr
145                 150                 155                 160

Pro Trp Ala Leu His Arg Met Gly Asn Pro Ser Asn Pro Ala Tyr Met
                165                 170                 175

Pro Val Ile His Ser Arg Phe Pro Val Lys Met Asn Phe Phe Gln Arg
            180                 185                 190

Met Ile Asn Thr Gly Trp His Leu Tyr Phe Leu Tyr Met Tyr Phe Tyr
        195                 200                 205

Tyr Gly Asn Gly Glu Asp Ala Asn Lys Met Ala Arg Lys Phe Phe Gly
    210                 215                 220

Asn Asp Met Pro Asp Ile Asn Glu Met Val Phe Asn Thr Ser Leu Leu
225                 230                 235                 240

Phe Val Asn Thr His Phe Ser Val Asp Met Pro Tyr Pro Leu Val Pro
                245                 250                 255

Asn Cys Ile Glu Ile Gly Gly Ile His Val Lys Glu Pro Gln Pro Leu
            260                 265                 270

Pro Leu Glu Ile Gln Lys Phe Met Asp Glu Ala Glu His Gly Val Ile
        275                 280                 285

Phe Phe Thr Leu Gly Ser Met Val Arg Thr Ser Thr Phe Pro Asn Gln
    290                 295                 300

```
Thr Ile Gln Ala Phe Lys Glu Ala Phe Ala Glu Leu Pro Gln Arg Val
305                 310                 315                 320

Leu Trp Lys Phe Glu Asn Glu Asn Glu Asp Met Pro Ser Asn Val Leu
            325                 330                 335

Ile Arg Lys Trp Phe Pro Gln Asn Asp Ile Phe Gly His Lys Asn Ile
                340                 345                 350

Lys Ala Phe Ile Ser His Gly Gly Asn Ser Gly Ala Leu Glu Ala Val
            355                 360                 365

His Phe Gly Val Pro Ile Ile Gly Ile Pro Leu Phe Tyr Asp Gln Tyr
        370                 375                 380

Arg Asn Ile Leu Ser Phe Val Lys Glu Gly Val Ala Val Leu Leu Asp
385                 390                 395                 400

Val Asn Asp Leu Thr Lys Asp Asn Ile Leu Ser Ser Val Arg Thr Val
                405                 410                 415

Val Asn Asp Lys Ser Tyr Ser Glu Arg Met Lys Ala Leu Ser Gln Leu
            420                 425                 430

Phe Arg Asp Arg Pro Met Ser Pro Leu Asp Thr Ala Val Tyr Trp Thr
        435                 440                 445

Glu Tyr Val Ile Arg His Arg Gly Ala His His Leu Lys Thr Ala Gly
450                 455                 460

Ala Phe Leu His Trp Tyr Gln Tyr Leu Leu Leu Asp Val Ile Thr Phe
465                 470                 475                 480

Leu Leu Val Thr Phe Cys Ala Phe Cys Phe Ile Val Lys Tyr Ile Cys
                485                 490                 495

Lys Ala Leu Ile His His Tyr Trp Ser Ser Lys Ser Glu Lys Leu
            500                 505                 510

Lys Lys Asn
        515

<210> SEQ ID NO 3
<211> LENGTH: 1548
<212> TYPE: DNA
<213> ORGANISM: Artificial Sequence
<220> FEATURE:
<223> OTHER INFORMATION: Yeast Optimized Sequence

<400> SEQUENCE: 3
atggaattca gattgttgat attggccttg ttctccgtat tgatgtctac ctctaatggt      60
gccgaaatct ggctttatt ccctattcat ggtatatcta actacaacgt agctgaagca     120
ttgttgaaga ctttggctaa cagaggtcac aacgttaccg ttgtaacttc atttccacaa     180
aagaaaccag ttcctaattt gtacgaaatt gatgtatcag gtgcaaaggg tttagccaca     240
aactccatcc atttcgaaag attgcaaacc atcatccaag atgtcaagag taacttcaag     300
aacatggtta gattgtctag aacatactgt gaaatcatgt tctcagaccc aagagttttg     360
aacatcagag ataaaaagtt tgacttggtt ataaacgccg tattcggttc agattgcgac     420
gctggttttg catggaaaag tcaagctcct ttaatatcta tcttgaatgc cagacataca     480
ccatgggctt tgcacagaat gggtaatcct tccaacccag catatatgcc tgtaatccat     540
agtagattcc cagtcaagat gaatttcttt caaagaatga taaacaccgg ttggcactta     600 tacttttgt acatgtactt ctactacggt aatggtgaag atgctaacaa aatggcaaga     660
aagtttttcg gtaatgatat gcctgacata aacgaaatgg ttttaacac tccttgttg     720 ttcgtaaaca ctcatttcag tgtcgatatg ccataccctt tagtcccaaa ctgtatcgaa     780
atcggtggta tccatgttaa ggaaccacaa cctttgccat ggaaatcca aagtttatg     840
```

```
gatgaagcag aacatggtgt aatcttttc accttgggta gtatggtcag aacttctaca      900
ttccctaatc aaactattca agcctttaaa gaagccttcg ctgaattacc acaaagagtt      960
ttgtggaagt tcgaaaacga aaacgaagat atgccttcca acgttttgat cagaaagtgg     1020
ttcccacaaa acgacatctt cggtcataag aacatcaagg ctttcatttc acacggtggt     1080
aattccggtg ccttggaagc tgtccatttc ggtgttccta tcataggtat cccattgttt     1140
tatgatcaat acagaaacat cttgtctttc gttaaagaag gtgtagctgt cttgttggat     1200
gtaaacgact taactaagga taacatcttg tcttcagtta gaacagtcgt taacgacaag     1260
tcatactccg aaagaatgaa ggcattgtct caattgttta gagatagacc tatgtcacca     1320
ttagacacag ctgttattg gaccgaatac gtaattagac atagaggtgc acatcactta     1380
aaaactgcag gtgccttttt gcactggtat caatacttgt tgttggatgt catcacattt     1440 tgttggtta cattctgtgc attctgcttc atcgttaagt acatctgcaa ggccttaatc     1500
catcactact ggtccagttc taaatctgaa aagttgaaaa agaattaa                 1548
```

<210> SEQ ID NO 4
<211> LENGTH: 492
<212> TYPE: PRT
<213> ORGANISM: Sorghum bicolor

<400> SEQUENCE: 4

```
Met Gly Ser Asn Ala Pro Pro Pro Thr Pro His Val Val Leu Val
1               5                   10                  15

Pro Phe Pro Gly Gln Gly His Val Ala Pro Leu Met Gln Leu Ala Arg
            20                  25                  30

Leu Leu His Ala Arg Gly Ala Arg Val Thr Phe Val Tyr Thr Gln Tyr
        35                  40                  45

Asn Tyr Arg Arg Leu Leu Arg Ala Lys Gly Glu Ala Ala Val Arg Pro
    50                  55                  60

Pro Ala Thr Ser Ser Ala Arg Phe Arg Ile Glu Val Ile Asp Asp Gly
65                  70                  75                  80

Leu Ser Leu Ser Val Pro Gln Asn Asp Val Gly Gly Leu Val Asp Ser
                85                  90                  95

Leu Arg Lys Asn Cys Leu His Pro Phe Arg Ala Leu Leu Arg Arg Leu
            100                 105                 110

Gly Gln Glu Val Glu Gly Gln Asp Ala Pro Pro Val Thr Cys Val Val
        115                 120                 125

Gly Asp Val Val Met Thr Phe Ala Ala Ala Ala Arg Glu Ala Gly
    130                 135                 140

Ile Pro Glu Val Gln Phe Phe Thr Ala Ser Ala Cys Gly Leu Leu Gly
145                 150                 155                 160

Tyr Leu His Tyr Gly Glu Leu Val Glu Arg Gly Leu Val Pro Phe Arg
                165                 170                 175

Asp Ala Ser Leu Leu Ala Asp Asp Tyr Leu Asp Thr Pro Leu Glu
            180                 185                 190

Trp Val Pro Gly Met Ser His Met Arg Leu Arg Asp Met Pro Thr Phe
        195                 200                 205

Cys Arg Thr Thr Asp Pro Asp Asp Val Met Val Ser Ala Thr Leu Gln
    210                 215                 220

Gln Met Glu Ser Ala Ala Gly Ser Lys Ala Leu Ile Leu Asn Thr Leu
225                 230                 235                 240

Tyr Glu Leu Glu Lys Asp Val Val Asp Ala Leu Ala Ala Phe Phe Pro
```

-continued

```
                245                 250                 255
Pro Ile Tyr Thr Val Gly Pro Leu Ala Glu Val Ile Ala Ser Ser Asp
            260                 265                 270

Ser Ala Ser Ala Gly Leu Ala Ala Met Asp Ile Ser Ile Trp Gln Glu
        275                 280                 285

Asp Thr Arg Cys Leu Ser Trp Leu Asp Gly Lys Pro Ala Gly Ser Val
    290                 295                 300

Val Tyr Val Asn Phe Gly Ser Met Ala Val Met Thr Ala Ala Gln Ala
305                 310                 315                 320

Arg Glu Phe Ala Leu Gly Leu Ala Ser Cys Gly Ser Pro Phe Leu Trp
                325                 330                 335

Val Lys Arg Pro Asp Val Val Glu Gly Glu Val Leu Leu Pro Glu
            340                 345                 350

Ala Leu Leu Asp Glu Val Ala Arg Gly Arg Gly Leu Val Val Pro Trp
        355                 360                 365

Cys Pro Gln Ala Ala Val Leu Lys His Ala Ala Val Gly Leu Phe Val
    370                 375                 380

Ser His Cys Gly Trp Asn Ser Leu Leu Glu Ala Thr Ala Ala Gly Gln
385                 390                 395                 400

Pro Val Leu Ala Trp Pro Cys His Gly Glu Gln Thr Thr Asn Cys Arg
                405                 410                 415

Gln Leu Cys Glu Val Trp Gly Asn Gly Ala Gln Leu Pro Arg Glu Val
            420                 425                 430

Glu Ser Gly Ala Val Ala Arg Leu Val Arg Glu Met Met Val Gly Asp
        435                 440                 445

Leu Gly Lys Glu Lys Arg Ala Lys Ala Glu Trp Lys Ala Ala Ala
    450                 455                 460

Glu Ala Ala Ala Arg Lys Gly Gly Ala Ser Trp Arg Asn Val Glu Arg
465                 470                 475                 480

Val Val Asn Asp Leu Leu Leu Val Gly Gly Lys Gln
                485                 490
```

<210> SEQ ID NO 5
<211> LENGTH: 471
<212> TYPE: PRT
<213> ORGANISM: Oryza sativa

<400> SEQUENCE: 5

```
Met Pro Ser Ser Gly Asp Ala Ala Gly Arg Arg Pro His Val Val Leu
1               5                   10                  15

Ile Pro Ser Ala Gly Met Gly His Leu Val Pro Phe Gly Arg Leu Ala
            20                  25                  30

Val Ala Leu Ser Gly His Gly Cys Asp Val Ser Leu Val Thr Val
        35                  40                  45

Leu Pro Thr Val Ser Thr Ala Glu Ser Lys His Leu Asp Ala Leu Phe
    50                  55                  60

Asp Ala Phe Pro Ala Val Arg Arg Leu Asp Phe Glu Leu Ala Pro Phe
65                  70                  75                  80

Asp Ala Ser Glu Phe Pro Gly Ala Asp Pro Phe Phe Leu Arg Phe Glu
                85                  90                  95

Ala Met Arg Arg Ser Ala Pro Leu Leu Gly Pro Leu Leu Thr Gly Ala
            100                 105                 110

Gly Ala Ser Ala Leu Ala Thr Asp Ile Ala Leu Thr Ser Val Val Ile
        115                 120                 125
```

-continued

```
Pro Val Ala Lys Glu Gln Gly Leu Pro Cys His Ile Leu Phe Thr Ala
    130                 135                 140
Ser Ala Ala Met Leu Ser Leu Cys Ala Tyr Phe Pro Thr Tyr Leu Asp
145                 150                 155                 160
Ala Asn Ala Gly Gly Gly Gly Val Gly Asp Val Asp Ile Pro Gly
                165                 170                 175
Val Tyr Arg Ile Pro Lys Ala Ser Ile Pro Gln Ala Leu His Asp Pro
            180                 185                 190
Asn His Leu Phe Thr Arg Gln Phe Val Ala Asn Gly Arg Ser Leu Thr
                195                 200                 205
Ser Ala Ala Gly Ile Leu Val Asn Thr Phe Asp Ala Leu Glu Pro Glu
210                 215                 220
Ala Val Ala Ala Leu Gln Gln Gly Lys Val Ala Ser Gly Phe Pro Pro
225                 230                 235                 240
Val Phe Ala Val Gly Pro Leu Leu Pro Ala Ser Asn Gln Ala Lys Asp
                245                 250                 255
Pro Gln Ala Asn Tyr Met Glu Trp Leu Asp Ala Gln Pro Ala Arg Ser
            260                 265                 270
Val Val Tyr Val Ser Phe Gly Ser Arg Lys Ala Ile Ser Arg Glu Gln
        275                 280                 285
Leu Arg Glu Leu Ala Ala Gly Leu Glu Gly Ser Gly His Arg Phe Leu
    290                 295                 300
Trp Val Val Lys Ser Thr Val Val Asp Arg Asp Asp Ala Ala Glu Leu
305                 310                 315                 320
Gly Glu Leu Leu Asp Glu Gly Phe Leu Glu Arg Val Glu Lys Arg Gly
                325                 330                 335
Leu Val Thr Lys Ala Trp Val Asp Gln Glu Glu Val Leu Lys His Glu
            340                 345                 350
Ser Val Ala Leu Phe Val Ser His Cys Gly Trp Asn Ser Val Thr Glu
        355                 360                 365
Ala Ala Ala Ser Gly Val Pro Val Leu Ala Leu Pro Arg Phe Gly Asp
    370                 375                 380
Gln Arg Val Asn Ser Gly Val Val Ala Arg Ala Gly Leu Gly Val Trp
385                 390                 395                 400
Ala Asp Thr Trp Ser Trp Glu Gly Glu Ala Gly Val Ile Gly Ala Glu
                405                 410                 415
Glu Ile Ser Glu Lys Val Lys Ala Ala Met Ala Asp Glu Ala Leu Arg
            420                 425                 430
Met Lys Ala Ala Ser Leu Ala Glu Ala Ala Lys Ala Val Ala Gly
        435                 440                 445
Gly Gly Ser Ser His Arg Cys Leu Ala Glu Phe Ala Arg Leu Cys Gln
    450                 455                 460
Gly Gly Thr Cys Arg Thr Asn
465                 470
```

GLYCOSYLTRANSFERASE GLYCOSYLATING FLAVOKERMESIC ACID AND/OR KERMESIC ACID

CROSS REFERENCE TO RELATED APPLICATION

This application is a continuation of U.S. application Ser. No. 15/105,673 filed Jun. 17, 2016, which is a national stage of International Application No. PCT/EP2014/078540 filed Dec. 18, 2014, which claims the foreign priority benefit of EP 13198110.2 filed Dec. 18, 2013, which are each hereby incorporated by reference.

FIELD OF THE INVENTION

The present invention relates to an isolated glycosyltransferase (GT) polypeptide capable of: (I): conjugating glucose to flavokermesic acid (FK); and/or (II): conjugating glucose to kermesic acid (KA) and the use of this GT to make e.g. Carminic acid.

BACKGROUND OF THE INVENTION

The natural pigment carminic acid is one of the most frequently used colorants of food, medicine, cosmetics and textiles.

Carminic acid is a colorant, which can be extracted from the female insect bodies of *Dactylopius coccus costa* (alternative name *Coccus cacti* L.). The insects live on *Nopalea coccinellifera, Opuntia fidus indica* and other plants of the family Cactaceae cultivated for instance in the desert areas of Mexico, Central and South America and Canary Islands. Depending on the pH the colorant may be a color in a spectrum from orange over red to purple and is generally known as cochineal or cochineal color. Carmine colorant is widely used in foods and beverages.

As known in the art *Porphyrophora polonica* is also producing carminic acid and was cultured for production of carminic acid in e.g. Poland.

In relation to current industrial relevant production, carminic acid is harvested by extraction from the insect's dried bodies with water or alcohol.

The insects (*Dactylopius coccus*) are cultured on cacti and the supply may therefore be relatively expensive and subject to undesirable variations and price fluctuations.

In order to try to resolve the problem of undesirable variations and price fluctuations—U.S. Pat. No. 5,424,421 (European Colour, published 1995) describes chemical synthesis of carminic acid by a route of synthesis involving different intermediates.

As discussed in e.g. WO2006/056585A1 (Chr. Hansen A/S)—during the aqueous based extraction of carminic acid from the insect, an amount of insect protein is also released from the insect and will be contained in the color extract and it has been reported that the cochineal insect proteins could create some allergy related problems. In WO2006/056585A1 a special process to reduce the amount of insect protein from the insect extract solution is described—however, the final produced color composition/product of WO2006/056585A1 will still comprise some amounts *Dactylopius coccus* costa insect proteins.

The structure of carminic acid is shown in FIG. 1—as can be seen it is a so-called C-glucoside (i.e. wherein the glucose is joined/conjugated to the aglucon by a carbon-carbon linkage).

According to the art—the term "aglycon" denotes the non-carbohydrate part of the corresponding glycosylated form of the aglycon. When the sugar is glucose the aglycon may be termed aglucon.

According to the art—the term "glycoside" denotes a compound which by hydrolysis results in a sugar and a non-sugar (aglycon) residue, e.g. glucosides can give glucose, galactosides can give galactose. As shown in FIG. 1—hydrolysis of the C-glucoside carminic acid results in glucose and the aglucon kermesic acid (KA).

The in vivo insect (*Dactylopius coccus*) biosynthetic pathway involved in carmine production is currently not described in details—accordingly, based on the prior art the skilled person does not know which compound is the aglucon during the in vivo *Dactylopius coccus* biosynthetic production of carminic acid.

Analysis of *D. coccus* has shown that a broad range of compounds related to carminic acid are present in extract from *D. coccus* and numerous of these compounds could in principle be glucosylated during the in vivo *Dactylopius coccus* biosynthetic production of carminic acid.

For instance, the article of Stathopoulou et al (Analytica Chimica Acta 804 (2013) 264-272) describes six new anthraquinones that are present in extract from *D. coccus* and any of these six new anthraquinones (see e.g. FIG. 1 of the article) could in principle be the molecule which is glucosylated during the in vivo *Dactylopius coccus* biosynthetic production of carminic acid.

Furthermore, and as known in the art, the primary glucosylated compound formed during the in vivo biosynthetic production of the glucoside end product may be an unstable intermediate compound that will not be identified in an isolated extract from *D. coccus* as e.g. analyzed in the above discussed article of Stathopoulou et al.

Based on the prior art, it could be speculated that a relevant primary glucosylated compound during the in vivo *Dactylopius coccus* biosynthetic production of carminic acid could e.g. be an unstable intermediate polyketide compound with around the same number of carbon atoms as e.g. flavokermesic acid.

According to the art—the term "glycosyltransferase" (GT) denotes a glycosyltransferase enzyme capable of transferring a sugar from an activated nucleotide sugar to an aglycon to form a glycoside.

A herein relevant DNA or amino acid sequence of a glycosyltransferase involved in the in vivo insect (*Dactylopius coccus*) biosynthetic pathway of carminic acid is not explicitly described in the prior art.

As known in the art, for insects that accumulate low molecular weight chemicals the relevant biosynthetic pathway genes are sometimes not present in the insect genome. For instance, some insects take up glycosides from the plants they feed on—see e.g. the article of Zagrobelny et al (Cyanogenic glucosides and plant-insect interactions; Phytochemistry. 2004 February; 65(3):293-306) or the article of Geuder et al (Journal of Chemical Ecology, Vol. 23, No. 5, 1997). Also, the relevant biosynthetic pathway genes are sometimes found in the microorganisms living in the insects, see e.g. the article of Genta et al, (Potential role for gut microbiota in cell wall digestion and glucoside detoxification in *Tenebrio molitor* larvae), Journal of Insect Physiology 52 (2006) 593-601.

*Dactylopius coccus* insects feed on cactus plants and it could be that *D. coccus* insects (like other insects) take up relevant glycosides from the cactus they feed on Accordingly, based on the prior art the skilled person could not know if the genome of *Dactylopius coccus* actually would comprise a gene encoding a glycosyltransferase involved in the in vivo biosynthetic pathway leading to carminic acid.

WO2004/111254A1 (Poalis A/S) describes in vivo production of a glucosylated form of vanillin in e.g. eukaryotic cell yeast cells and/or prokaryotic E. coli cells by using a glucosyltransferase for conjugating glucose to the vanillin aglucon in vivo within a microorganism cell. Natural vanillin is obtained from the plant vanilla bean. Accordingly, in the prior art successful in vivo production has been described in microorganism cells of plant glycoside compounds (such as e.g. vanillin glucoside).

SUMMARY OF THE INVENTION

The problem to be solved by the present invention relates to the provision of a glycosyltransferase (GT) involved in a biosynthetic pathway that may lead to carminic acid and the use of this glycosyltransferase to make e.g. carminic acid.

As discussed in working examples herein—the present inventors sequenced the entire genome and transcriptome (i.e. set of RNA molecules including mRNA) of *Dactylopius coccus* and microbial symbionts.

The identified oligonucleotide sequences obtained from the genome and transcriptome were analyzed for similarity to public known C-glycosyltransferase sequences and the result was negative. None of the identified gene sequences of the genome/transcriptome showed significant similarity to publicly known C-glycosyltransferase sequences.

As discussed above—based on the prior art the skilled person could not know if the genome of *Dactylopius coccus* actually would comprise a gene encoding a glycosyltransferase involved in the in vivo biosynthetic pathway leading to carminic acid. However, the present inventors continued to investigate the matter.

As discussed in working examples herein—the present inventors identified a *Dactylopius coccus* extract (including extracts of the endosymbionts present in *D. coccus*) with relevant GT activity and by a combination of relevant purification and testing steps the inventors were finally able to obtain a relatively pure fraction/composition wherefrom it was possible to obtain several partial amino acid sequences of putative GT enzyme candidates.

The partial amino acid sequences of these enzyme candidates were compared to the identified gene sequences of the transcriptome and after further detailed work, a sequence encoding a glycosyltransferase enzyme sequence was identified—the polynucleotide sequence encoding this isolated/cloned novel glycosyltransferase is shown in SEQ ID NO: 1 and the polypeptide amino acid sequence is shown in SEQ ID NO: 2.

The glycosyltransferase enzyme of SEQ ID NO: 2 may be termed "DcUGT2".

It is believed that the described isolated/cloned glycosyltransferase is the first described insect derived glycosyltransferase. As described, the identified gene sequences of the *Dactylopius coccus* transcriptome were analyzed for similarity to relevant public known glycosyltransferase sequences and the result was negative.

The present inventors found, that the publicly known prior art glycosyltransferase sequences have less than 45% identity to the novel glycosyltransferase polypeptide sequence shown as SEQ ID NO: 2.

As discussed in working examples herein—the present inventors tested the activity of the isolated/cloned novel glycosyltransferase and found that it was able to conjugate glucose to the aglycons flavokermesic acid (FK) and kermesic acid (KA)—see FIG. 1. Analysis of the glucosylated product showed that among the many potential O- and C-glucoside products potentially formed only a single glucoside product was formed with each of the two substrates. The analysis showed that each of the products were C-glucosylated at position 7 of the anthraquinone structure, more precisely 7-α-D-Glucopyranosyl-9,10-dihydro-3,6,8-trihydroxy-1-methyl-9,10-dioxoanthracenecarboxylic acid (DcII—see FIG. 1) and 7-α-D-Glucopyranosyl-9,10-dihydro-3,5,6,8-tetrahydroxy-1-methyl-9,10-dioxoanthracenecarboxylic acid (carminic acid—see FIG. 1) by the GT when UDP-glucose was used as the sugar donor substrate.

The article of Gutmann et al (Pure Appl. Chem, 2013-07-09) describes that even though a number of C-glycosides have been isolated from natural sources, the enzymes responsible for their biosynthesis are only known in very few cases, and the biocatalytic approaches for C-glycoside production has yet to be established The article of Baig et al (Angew Chem Int Ed Engl. 2006 Nov. 27; 45(46):7842-6) describes the glycosyltransferase (GT) termed UrdGT2 and explains that it is able to conjugate a sugar to a number of aglycons that may herein be considered relatively similar to flavokermesic acid (FK) and kermesic acid (KA).

Accordingly, it may be said that UrdGT2 prima facie would be a qualified guess for a GT that could be capable of conjugating sugar to flavokermesic acid (FK) and/or kermesic acid (KA).

As discussed in working Example herein—the present inventors cloned the UrdGT2 and tested it for flavokermesic acid (FK) and/or kermesic acid (KA) GT activity and it was found that the UrdGT2 was able to use UDP-glucose as a sugar donor, but UrdGT2 did not glucosylate any of the tested putative aglycons—i.e. no GT activity was identified in relation to these aglycons.

The UrdGT2 has around 15-20% amino acid identity with SEQ ID NO:2 disclosed herein.

Based on both publicly known GT sequences and not publicly known GT sequences—the present inventors made different detailed sequence alignment investigations. Based on these sequence alignment investigations—it is believed that amino acids 20 to around 468 of SEQ ID NO:2 comprise the essential parts of the catalytic domain. Based on these sequence alignment investigations—it is believed that amino acids from around 291 to around 383 of SEQ ID NO:2 comprise the so-called activated nucleotide sugar binding site.

Based on these sequence alignment investigations—it is believed that amino acids from around 1 to around 20 of SEQ ID NO:2 comprise the so-called signal peptide and it is believed that this signal peptide may be removed without significantly affecting the herein relevant GT activity of the enzyme.

Furthermore, it is believed that the activated nucleotide sugar binding site may be substituted by similar (e.g. prior art known) GT activated nucleotide sugar binding site sequences—such as e.g. the activated nucleotide sugar binding site as described in Radominska-Pandya A, Bratton S M, Redinbo M R, Miley M J. Drug Metab Rev. 2010 February; 42(1):133-44) and Plant Physiology, November 2008, Vol. 148, pp. 1295-1308.

Accordingly, a first aspect of the present invention relates to an isolated glycosyltransferase polypeptide capable of:

(I): conjugating glucose to flavokermesic acid (FK); and/or (II): conjugating glucose to kermesic acid (KA);

and wherein the glycosyltransferase polypeptide is at least one polypeptide selected from the group consisting of:
(a) a polypeptide comprising an amino acid sequence which has at least 70% identity with amino acids 1 to 515 of SEQ ID NO:2;
(b) a polypeptide comprising an amino acid sequence which has at least 70% identity with amino acids 20 to 468 of SEQ ID NO:2;
(c) a polypeptide which is encoded by a polynucleotide that hybridizes under at least medium stringency conditions with (i) nucleotides 1 to 1548 of SEQ ID NO:1 or (ii) a complementary strand of (i); and
(d) a fragment of amino acids 1 to 515 of SEQ ID NO:2, which has the glycosyltransferase activity as specified in (I) and/or (II).

As understood by the skilled person in the present context—the term "a glycosyltransferase polypeptide capable of" of the first aspect relates to that the glycosyltransferase shall be capable of performing the glycosyltransferase (I) and/or (II) activity—but it may or may not also be capable of performing other glycosyltransferase activities.

As understood by the skilled person in the present context—the disclosure of the herein described novel glycosyltransferase sequence is an important tool to identify similar glycosyltransferases in e.g. other insects than *Dactylopius coccus* and without being limited to theory—it is believed that a sequence with at least 70% identity with SEQ ID NO:2 would be a plausible good candidate for a another herein relevant glycosyltransferase.

A second aspect of the present invention relates to an isolated polynucleotide comprising a nucleotide sequence which encodes the polypeptide of the first aspect and/or herein relevant embodiments thereof.

A third aspect of the present invention relates to a nucleic acid construct comprising the isolated polynucleotide of the second aspect and/or herein relevant embodiments thereof operably linked to one or more control sequences that direct the production of the polypeptide in an expression host.

A fourth aspect of the present invention relates to a recombinant expression vector comprising the nucleic acid construct of the third aspect and/or herein relevant embodiments thereof.

A fifth aspect of the present invention relates to a recombinant host cell comprising the nucleic acid construct of the third aspect and/or herein relevant embodiments thereof.

As discussed above—based on the prior art the skilled person does not know which compound is the primary glycosylated compound during the biosynthetic production of carminic acid in vivo in *Dactylopius coccus*.

It has been shown that *D. coccus* contains a GT able to C-glycosylate flavokermesic acid (FK) and/or kermesic acid (KA).

It is evident that this important knowledge is sufficient in order to e.g. produce carminic acid without the need to make an extraction from insects and thereby be able to make a carminic acid color composition/product essentially free of e.g. unwanted *Dactylopius coccus* costa insect proteins.

Since the skilled person did not know which compound is glycosylated during the in vivo *Dactylopius coccus* biosynthetic production of carminic acid it was actually unknown to the skilled person if there in nature actually existed a glycosyltransferase capable of C-glycosylating flavokermesic acid aglycon and/or the kermesic acid aglycon.

It is believed that the herein disclosed novel glycosyltransferase represents the first isolated glycosyltransferase capable of glycosylating flavokermesic acid aglycon and/or kermesic acid.

Accordingly, based on the technical disclosure herein—it is believed that the skilled person would be able to identify other suitable glycosyltransferases capable of glycosylating flavokermesic acid (FK) and/or kermesic acid (KA).

The skilled person would appreciate that one way to try to identify if an organism/plant would comprise a relevant glycosyltransferase would be to contact relevant aglycons (i.e. FK and/or KA) to the organism/plant (in vivo and/or in vitro) and then measure if the organism/plant produces relevant FK and/or KA glycosides.

As understood herein, if the organism/plant produces relevant FK and/or KA glycosides then the organism/plant will comprise a relevant glycosyltransferase—i.e. a glycosyltransferase which is capable of glycosylating flavokermesic acid in order to produce flavokermesic acid glycoside; and/or capable of glycosylating kermesic acid in order to produce kermesic acid glycoside.

As discussed below—based on the strategy above, the present inventors found that relevant glycosyltransferases may be identified in Aloe plants, *Haworthia* plants, *Sorghum* or rice plants.

Accordingly, a sixth aspect of the present invention relates to a method for producing flavokermesic acid (FK)glycoside and/or kermesic acid (KA) glycoside, wherein the method comprises following steps:
(A): contacting in vitro or in vivo in a recombinant host cell comprising a glycosyltransferase gene encoding a glycosyltransferase:
(a1): flavokermesic acid (FK) with a glycosyltransferase capable of glycosylating the flavokermesic acid under suitable conditions wherein there is produced the flavokermesic acid glycoside; and/or
(a2): kermesic acid (KA) with a glycosyltransferase capable of glycosylating the kermesic acid under suitable conditions wherein there is produced the kermesic acid glycoside.

The term "recombinant host cell" should herein be understood according to the art. As known in the art, recombinant polynucleotide (e.g. DNA) molecules are polynucleotide (e.g. DNA) molecules formed by laboratory methods of genetic recombination (such as molecular cloning) to bring together genetic material from multiple sources, creating sequences that would not otherwise be found in biological organisms. As understood by the skilled person—a recombinant host cell comprises recombinant polynucleotide (e.g. DNA) molecules and a recombinant host cell will therefore not be understood as covering a natural wildtype cell as such—such as e.g. a natural wildtype *Dactylopius coccus* cell.

Said in other words and as understood by the skilled person—for instance a natural wildtype *Dactylopius coccus* cell as such does not contain a recombinant glycosyltransferase gene encoding a glycosyltransferase.

It may be preferred that the recombinant host cell in step (A) is a recombinant host cell comprising a recombinant glycosyltransferase gene encoding a glycosyltransferase As discussed herein—in working Examples there was made a contacting in vitro of flavokermesic acid (FK) and/or kermesic acid (KA) with the glycosyltransferase of SEQ ID NO:2. It may be seen as routine work for the skilled person to perform such an in vitro contacting step.

The glycosyltransferase of SEQ ID NO:2 was recombinantly expressed in a yeast cell (see working Example)—accordingly, a recombinant yeast host cell comprising a recombinant glycosyltransferase gene encoding a glycosyltransferase of SEQ ID NO:2 was made.

It is believed that if flavokermesic acid (FK) and/or kermesic acid (KA) would be added under suitable conditions to a fermentation medium the FK and/or KA compound(s) would enter into e.g. yeast cells fermented in the medium—accordingly, if e.g. the yeast cells are recombinant yeast host cells comprising a recombinant glycosyltransferase gene encoding a glycosyltransferase then there would be made a contacting in vivo in a recombinant host cell of FK and/or KA with a glycosyltransferase.

In e.g. above discussed WO2004/111254A1 (Poalis A/S) such in vivo contacting of different aglycon compounds in different recombinant host cells were made and the skilled person would know how to perform such contacting in vivo in a recombinant host cell of a relevant aglycon (here flavokermesic acid (FK) and/or kermesic acid (KA)) and a recombinantly expressed glycosyltransferase.

As discussed above—it is believed that the herein disclosed novel glycosyltransferase represents the first time that there has been disclosed an isolated glycosyltransferase capable of glycosylating flavokermesic acid aglycon and/or kermesic acid aglycon.

It is believed that relevant partial sequences of herein disclosed novel glycosyltransferase of SEQ ID NO:2 may be recombinantly introduced into another glycosyltransferase sequence in order to construct a new hybrid glycosyltransferase sequence capable of glucosylating flavokermesic acid and/or kermesic acid. Such GTs with reduced $k_M$ or increased $V_{max}$ may prove important in securing rapid glucosylation of the substrates that may show toxic effects inhibiting yeast growth if accumulating at high levels (Esben Halkjaer Hansen et al. Phytochemistry 70(4): 473-482). Likewise, if so desired it is envisioned possible to modify the substrate specificity towards glucosylation of earlier pathway intermediates.

Accordingly, a further aspect of the present invention relates to a method for constructing a novel isolated hybrid glycosyltransferase polypeptide capable of:
(I): conjugating glucose to flavokermesic acid (FK); and/or
(II): conjugating glucose to kermesic acid (KA),
wherein the method comprises following steps:
(i): inserting a polynucleotide sequence encoding a fragment of an amino acid sequence which has at least 70% identity with amino acids 1 to 515 of SEQ ID NO:2 (preferably a fragment of an amino acid sequence which has at least 90% identity with amino acids 1 to 515 of SEQ ID NO:2, more preferably a fragment of an amino acid sequence which has at least 99% identity with amino acids 1 to 515 of SEQ ID NO:2) wherein the fragment comprises at least 75 amino acids (preferably at least 100 amino acids, more preferably at least 150 amino acids and even more preferably at least 468 amino acids), into another polynucleotide sequence derived from a glycosyltransferase in order to thereby construct a novel recombinant hybrid polynucleotide sequence;
(ii): expressing the novel hybrid polypeptide which is encoded by the novel recombinant hybrid polynucleotide sequence of step (i);
(iii): isolating the expressed novel hybrid polypeptide of step (ii);
(iv): testing if the isolated novel hybrid polypeptide of step (iii) is capable of:
(I): conjugating glucose to flavokermesic acid (FK); and/or
(II): conjugating glucose to kermesic acid (KA); and (v) if positive in test of step (iv) then has been constructed the novel isolated hybrid glycosyltransferase polypeptide capable of:
(I): conjugating glucose to flavokermesic acid (FK); and/or
(II): conjugating glucose to kermesic acid (KA).

DEFINITIONS

All definitions of relevant terms are in accordance with what would be understood by the skilled person in relation to the relevant technical context.

The term "aglycon" denotes non-carbohydrate part of the corresponding glycosylated form of the aglycon. When the sugar is glucose the aglycon may be termed aglucon. Further, when the sugar is glucose the term glucosylated may be used instead of glycosylated.

When the aglycon is glycosylated at a hydroxy group there is generally created a so-called O-glycosidic bond—i.e. a so-called O-Glycoside (or O-Glucoside if the sugar is glucose).

When the aglycon is glycosylated by a carbon-carbon linkage it may be termed a C-glycosidic bond—i.e. a so-called C-Glycoside (or C-Glucoside if the sugar is glucose).

The term "glycoside" denotes a compound which on hydrolysis can give a sugar and a non-sugar (aglycon) residue, e. g. glucosides can give glucose and galactosides can give galactose.

The term "glycosyltransferase" denotes an enzyme capable of conjugating a nucleotide activated sugar to a compound (e.g. an aglycon compound). The sugar may e.g. be D and L isomers of galactose, glucosamine, N-acetylglusamine, xylose, glucuronic acid, rhamnose, arabinose, mannose or glucose. Alternatively the sugar may be a carbohydrate derivative such as e. g. inositol, olivose, rhodinose and etc available as nucleotide diphosphates. Further the sugar may e.g. be a monosaccharide, a disaccharide or a trisaccharide. In the case of oligo- and polysaccharides the sugars are linked one by one, by e. g. involving use of one or several glycosyltransferases. If the sugar is glucose the glycosyltransferase may be termed a glucosyltransferase.

When the glycosyltransferase conjugates a nucleotide activated sugar to a compound via a C-glycosidic bond it may be termed a C-glycosyltransferase.

When the glycosyltransferase conjugates a sugar to an aglycon via an O-glycosidic bond it may be termed an O-glycosyltransferase.

The term "hybridizes" in relation to a polynucleotide which hybridizes under at least medium stringency conditions with (i) nucleotides 1 to 1548 of SEQ ID NO:1 or (ii) a complementary strand of (i) relates to the nucleotide sequence which hybridizes to a labeled nucleic acid probe corresponding to the nucleotide sequence shown in SEQ ID NO:1 or its complementary strand under medium to very high stringency conditions. Molecules to which the nucleic acid probe hybridizes under these conditions can be detected using e.g. X-ray film.

Herein relevant hybridization stringency conditions are stringency conditions that the skilled person normally would understand are relevant—i.e. for medium stringency conditions the conditions that skilled person would understand are medium stringency conditions. The skilled person knows relevant hybridization stringency conditions—see e.g. (J. Sambrook, E. F. Fritsch, and T. Maniatus, 1989, Molecular Cloning, A Laboratory Manual, 2d edition, Cold Spring Harbor, N.Y.).

According to the art—for long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

The term "in vitro" (Latin: in glass) relates to studies that are conducted using components of an organism that have been isolated from their usual biological surroundings in order to permit a more detailed or more convenient analysis than can be done with whole organisms. These experiments are commonly called "test tube experiments". In contrast, in vivo studies are those that are conducted with living organisms in their normal intact state.

The term "in vivo" (Latin for "within the living") relates to experimentation using a whole, living organism as opposed to a partial or dead organism, or an in vitro ("within the glass", e.g., in a test tube or petri dish) controlled environment.

The term "isolated polynucleotide" essentially relates herein to that the polynucleotide is isolated from its natural environment—said in other words that the polynucleotide preparation is essentially free of other polynucleotide material with which it is natively associated. The polynucleotide sequence encoding the herein described isolated/cloned novel glycosyltransferase is shown in SEQ ID NO: 1 and it was isolated from the insect *Dactylopius coccus*. Accordingly, as understood by the skilled person—the term isolated polynucleotide does not cover the polynucleotide of SEQ ID NO: 1 when it is naturally present in the genome of *Dactylopius coccus*. The term "isolated polynucleotide" essentially relates to that the isolated polynucleotide is in a form suitable for use within genetically engineered protein production systems. Thus, an isolated polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. The term "isolated polynucleotide" may herein alternatively be termed "cloned polynucleotide".

The term "isolated polypeptide" essentially relates herein to that the polypeptide is isolated from its natural environment. The novel glycosyltransferase polypeptide as shown in SEQ ID NO: 2 was isolated from the insect *Dactylopius coccus*. Accordingly, as understood by the skilled person—the term "isolated polypeptide" does not cover the glycosyltransferase polypeptide of SEQ ID NO: 2 when it is naturally present in the genome of *Dactylopius coccus*. The term "isolated polypeptide" denotes a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. The term "other polypeptide material with which it is natively associated" may in relation to the novel glycosyltransferase polypeptide as shown in SEQ ID NO: 2 be seen in relation to other polypeptide material with which it is natively associated in *Dactylopius coccus*. In some case—it may be preferred that the "isolated polypeptide" refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention. As known in the art control, sequences include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "recombinant expression vector" relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites.

The term "recombinant host cell" should herein be understood according to the art. As known in the art, recombinant polynucleotide (e.g. DNA) molecules are polynucleotide (e.g. DNA) molecules formed by laboratory methods of genetic recombination (such as molecular cloning) to bring together genetic material from multiple sources, creating sequences that would not otherwise be found in biological organisms. As understood by the skilled person—a recombinant host cell comprises recombinant polynucleotide (e.g. DNA) molecules and a recombinant host cell will therefore not be understood as covering a natural wildtype cell, such as e.g. a natural wildtype *Dactylopius coccus* cell.

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment).

For purposes of the present invention, the degree of sequence identity between two nucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment).

Embodiments of the present invention are described below, by way of examples only.

DRAWINGS

FIG. 1: Schematic presentation of the relevant glycosyltransferase activity of the herein described isolated/cloned novel glycosyltransferase of SEQ ID NO:2—as illustrated in the figure it was found to be able to conjugate glucose to the aglycons flavokermesic acid (FK) and kermesic acid (KA).

Figure 2A:
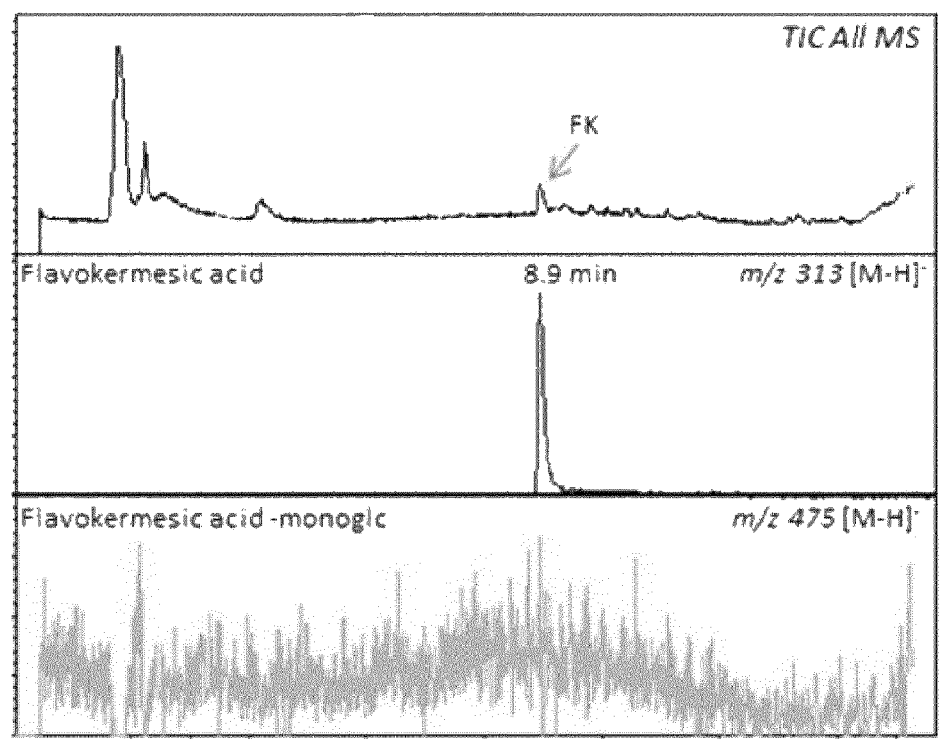

FIG. 2A: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from the *E. coli* strain Xjb (negative control) incubated with FK. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2B:
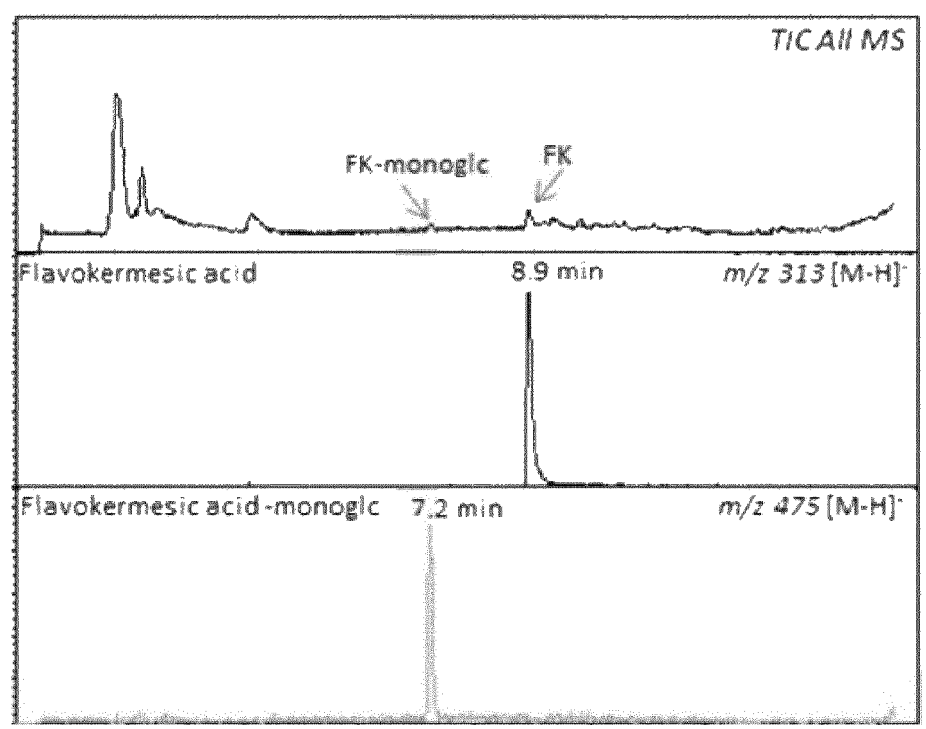

FIG. 2B: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from Xjb cells expressing OsCGT incubated with FK. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2C:
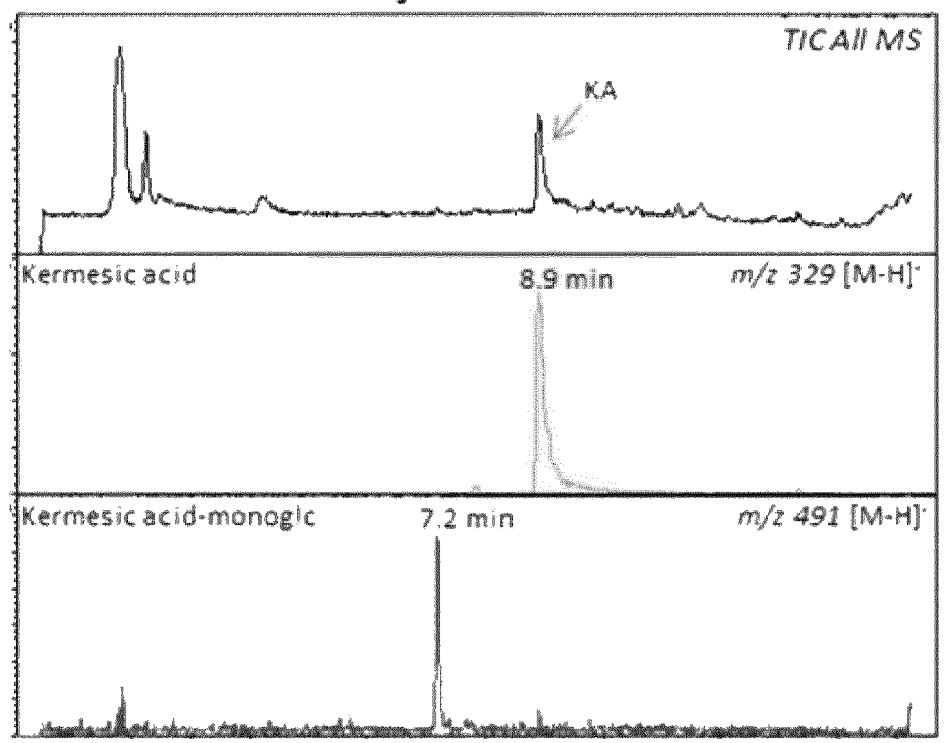

FIG. 2C: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from the *E. coli* strain Xjb (negative control) incubated with KA. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2D:
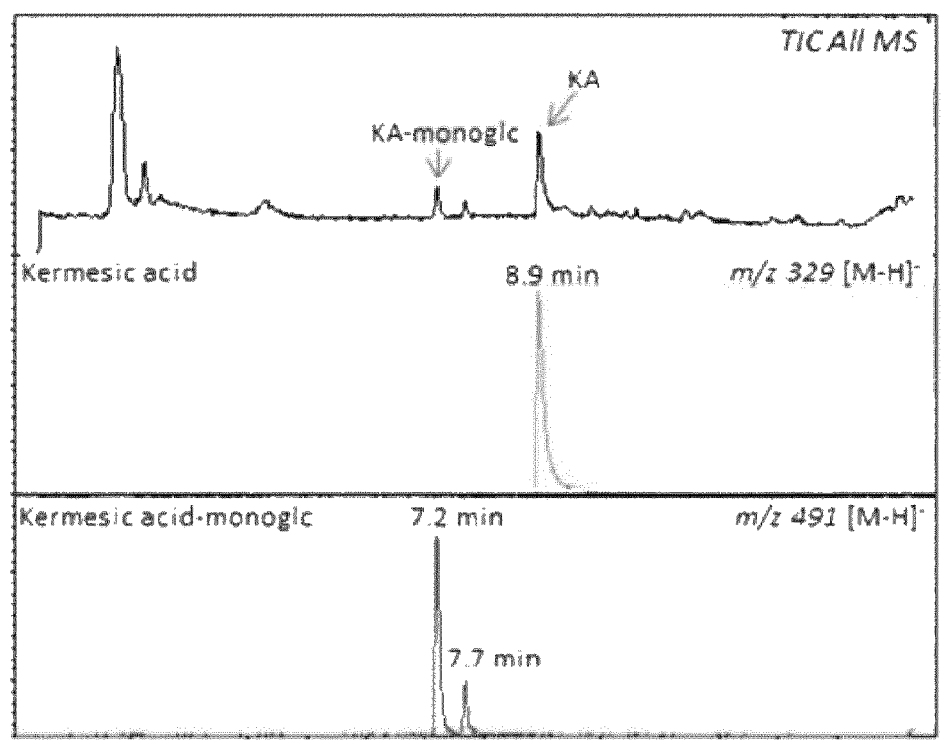

FIG. 2D: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from Xjb cells expressing OsCGT incubated with KA. The total ion chromatograms (TIC) and extracted ion chromatograms for m/z 313[M-H]$^-$, m/z 329 [M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2E:
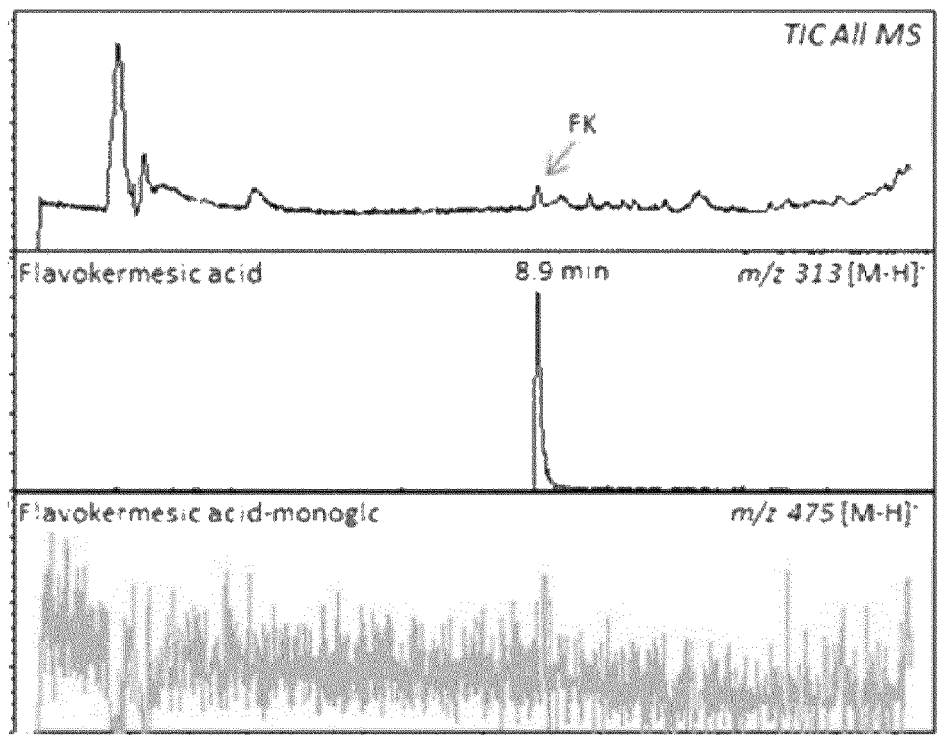

FIG. 2E: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from Xjb cells expressing SbUGT85B1 incubated with FK. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2F:
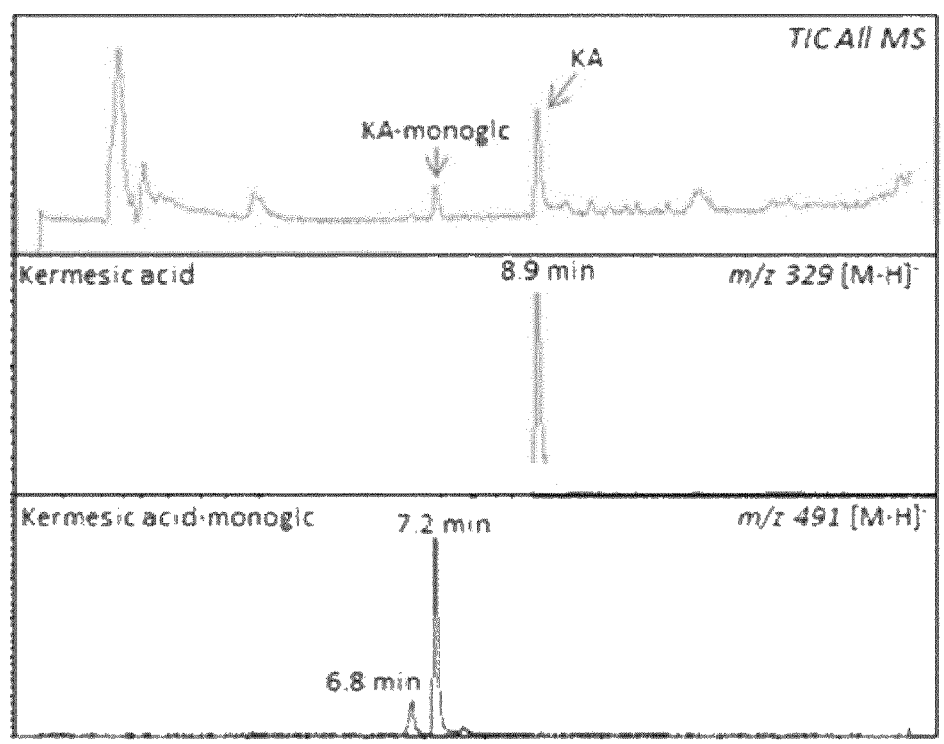

FIG. 2F: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). Crude lysate from Xjb cells expressing SbUGT85B1 incubated with KA. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2G:
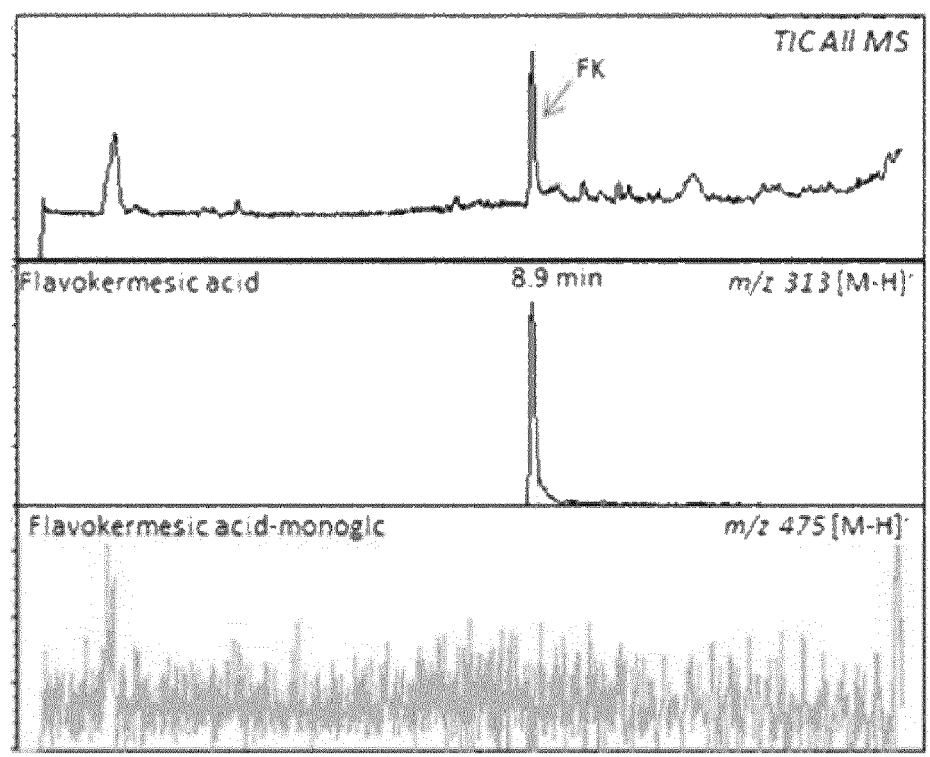

FIG. 2G: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). FK substrate alone. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

Figure 2H:
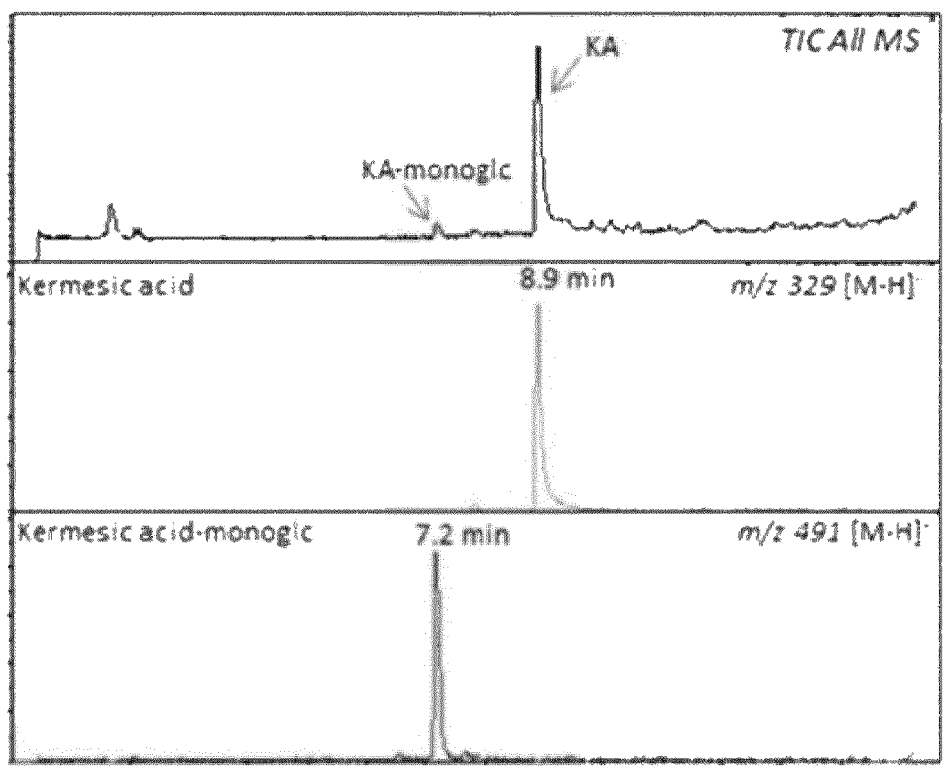

FIG. 2H: Production of glucosides of flavokermesic acid and kermesic acid using OsCGT and SbUGT85B1. LC-MS analyses of glucosylated products formed in assays containing UDP-glucose and flavokermesicc acid (FK) or kermesic acid (KA). KA substrate alone. The total ion chromatograms (TIC) and extracted ion chromatograms for m/z 313[M-H]$^-$, m/z 329[M-H]$^-$, m/z 475 [M-H]$^-$, m/z 491 [M-H]$^-$, corresponding to FK, KA, FK-monoglucoside, and KA-monoglucoside are indicated. Peak retention times are indicated in minutes.

DETAILED DESCRIPTION OF THE INVENTION

The present application includes a Sequence Listing which has been submitted in ASCII computer readable format (CFR) and in paper format, both via EFS-Web, and are hereby incorporated by reference in their entirety.

A Novel Isolated Glycosyltransferase Polypeptide as Described Herein

When there herein is referred to an isolated glycosyltransferase polypeptide as described herein there is referred to an isolated glycosyltransferase polypeptide of the first aspect of the invention and/or herein relevant embodiments thereof.

As discussed above—the term "isolated polypeptide" essentially relates to that the polypeptide is isolated from its natural environment. The herein described novel glycosyltransferase polypeptide as shown in SEQ ID NO: 2 was isolated from the insect *Dactylopius coccus*. Accordingly, as understood by the skilled person in the present context—the term "isolated polypeptide" does not cover the glycosyltransferase polypeptide of SEQ ID NO: 2 when it is naturally present in the genome of *Dactylopius coccus*.

Preferably, the isolated glycosyltransferase polypeptide as described herein denotes a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated.

As understood by the skilled person, the term "other polypeptide material with which it is natively associated" may in relation to the novel glycosyltransferase polypeptide as shown in SEQ ID NO: 2 be seen as relation to other polypeptide material with which it is natively associated in *Dactylopius coccus*.

In some case—it may be preferred that the isolated glycosyltransferase polypeptide as described herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Based on e.g. the sequence information disclosed herein—it is routine work for the skilled person to obtain an isolated glycosyltransferase polypeptide as described herein.

This may e.g. be done by recombinant expression in a suitable recombinant host cell according to procedures known in the art.

Accordingly, it is not believed necessary to describe such standard known recombinant expression procedures in many details herein.

Preferably, the isolated glycosyltransferase polypeptide as described herein is capable of:
(I): conjugating glucose to flavokermesic acid (FK); and
(II): conjugating glucose to kermesic acid (KA).

A preferred embodiment relates to wherein the glycosyltransferase polypeptide of the first aspect is:
(a) a polypeptide comprising an amino acid sequence which has at least 80% identity with amino acids 1 to 515 of SEQ ID NO:2; more preferably
(a) a polypeptide comprising an amino acid sequence which has at least 90% identity with amino acids 1 to 515 of SEQ ID NO:2; even more preferably
(a) a polypeptide comprising an amino acid sequence which has at least 95% identity with amino acids 1 to 515 of SEQ ID NO:2; and most preferably
(a) a polypeptide comprising an amino acid sequence which has at least 98% identity with amino acids 1 to 515 of SEQ ID NO:2.

It may be preferred that the glycosyltransferase polypeptide of the first aspect is a polypeptide comprising an amino acid sequence with amino acids 1 to 515 of SEQ ID NO:2.

A preferred embodiment relates to wherein the glycosyltransferase polypeptide of the first aspect is:
(b) a polypeptide comprising an amino acid sequence which has at least 80% identity with amino acids 20 to 468 of SEQ ID NO:2; more preferably
(b) a polypeptide comprising an amino acid sequence which has at least 90% identity with amino acids 20 to 468 of SEQ ID NO:2; even more preferably
(b) a polypeptide comprising an amino acid sequence which has at least 95% identity with amino acids 20 to 468 of SEQ ID NO:2; and most preferably
(b) a polypeptide comprising an amino acid sequence which has at least 98% identity with amino acids 20 to 468 of SEQ ID NO:2.

It may be preferred that the glycosyltransferase polypeptide of the first aspect is a polypeptide comprising an amino acid sequence with amino acids 20 to 468 of SEQ ID NO:2.

A preferred embodiment relates to wherein the glycosyltransferase polypeptide of the first aspect is:
(c) a polypeptide which is encoded by a polynucleotide which hybridizes under at least medium-high stringency conditions with (i) nucleotides 1 to 1548 of SEQ ID NO:1 or (ii) a complementary strand of (i); more preferably
(c) a polypeptide which is encoded by a polynucleotide which hybridizes under at least high stringency conditions with (i) nucleotides 1 to 1548 of SEQ ID NO:1 or (ii) a complementary strand of (i); and even more preferably
(c) a polypeptide which is encoded by a polynucleotide which hybridizes under at least very stringency conditions with (i) nucleotides 1 to 1548 of SEQ ID NO:1 or (ii) a complementary strand of (i).

It is routine work for the skilled person to make a variant of an isolated glycosyltransferase polypeptide as described herein—i.e. a variant, wherein e.g. one or more amino acids of e.g. SEQ ID NO:2 have been modified/altered.

Further—as known to the skilled person if such variant changes are not too drastic it will be plausible that the enzyme would maintain its relevant GT activity.

A preferred embodiment relates to wherein the glycosyltransferase polypeptide of the first aspect is:
(a) a polypeptide comprising an amino acid sequence with amino acids 1 to 515 of SEQ ID NO:2 or a variant thereof, wherein the variant comprises an alteration at one or more (several) positions of SEQ ID NO:2 and wherein the variant comprises less than 50 alterations, more preferably less than 40 alterations, even more preferably less than 20 alterations and most preferably less than 10 alterations.

In a preferred embodiment the term "an alteration at one or more (several) positions of SEQ ID NO:2" refers to 1 to 10 alterations in SEQ ID NO:2.

According to the art—the term "variant" means herein a peptide having the relevant GT activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

In a preferred embodiment the glycosyltransferase polypeptide of the first aspect is a GT which is membrane bound or insoluble in water.

Isolated Polynucleotide Comprising a Nucleotide Sequence which Encodes the Glycosytransferase Polypeptide as Described Herein As discussed above—a second aspect of the present invention relates to an isolated polynucleotide comprising a nucleotide sequence which encodes the polypeptide of the first aspect and/or herein relevant embodiments thereof.

The term "isolated polynucleotide" may herein alternatively be termed "cloned polynucleotide".

As discussed above—the term "isolated polynucleotide" essentially relates to that the polynucleotide is isolated from its natural environment—said in other words that the polynucleotide preparation is essentially free of other polynucleotide material with which it is natively associated. The polynucleotide sequence encoding the described isolated/cloned novel glycosyltransferase is shown in SEQ ID NO: 1 and it was isolated from the insect *Dactylopius coccus*. Accordingly, as understood by the skilled person—the term isolated polynucleotide does not cover the polynucleotide of SEQ ID NO: 1 when it is naturally present in the genome of *Dactylopius coccus*.

The term "isolated polynucleotide" essentially relates to that the isolated polynucleotide is in a form suitable for use within genetically engineered protein production systems.

Thus, an isolated polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated.

Based on e.g. the sequence information disclosed herein—it is routine work for the skilled person to obtain an isolated polynucleotide as described herein.

This may e.g. be done by recombinant expression in a suitable recombinant host cell according to procedures known in the art.

Accordingly, it is not believed necessary to describe such standard known recombinant expression procedures in many details herein.

A Nucleic Acid Construct Comprising the Isolated Polynucleotide as Described Herein As discussed above—a third aspect of the present invention relates to a nucleic acid construct comprising the isolated polynucleotide of the second aspect and/or herein relevant embodiments thereof operably linked to one or more control sequences that direct the production of the polypeptide in an expression host.

According to the art—the term "nucleic acid construct" as used herein refers to a nucleic acid molecule, either single- or double-stranded, which is isolated from a naturally occurring gene or which is modified to contain segments of nucleic acids in a manner that would not otherwise exist in nature.

The term nucleic acid construct is synonymous with the term "expression cassette" when the nucleic acid construct contains the control sequences required for expression of a coding sequence of the present invention. As known in the art control sequences include all components, which are necessary or advantageous for the expression of a polynucleotide encoding a polypeptide of the present invention.

Based on e.g. the sequence information disclosed herein—it is routine work for the skilled person to make a relevant nucleic acid construct—for instance, based on the prior art the skilled person knows numerous different suitable control sequences for the expression of a polynucleotide encoding a polypeptide of the present invention.

Accordingly, it is not believed necessary to describe such standard known technical elements in many details herein.

A Recombinant Expression Vector Comprising the Nucleic Acid Construct as Described Herein As discussed above—a fourth aspect of the present invention relates to a recombinant expression vector comprising the nucleic acid construct of the third aspect and/or herein relevant embodiments thereof.

According to the art—the term "recombinant expression vector" relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites.

Based on e.g. the sequence information disclosed herein—it is routine work for the skilled person to make a relevant recombinant expression vector—for instance, based on the prior art the skilled person knows numerous different suitable promoter, and transcriptional and translational stop signals.

Accordingly, it is not believed necessary to describe such standard known technical elements in many details herein.

A Recombinant Host Cell Comprising the Nucleic Acid Construct as Described Herein As discussed above—a fifth aspect of the present invention relates to a recombinant host cell comprising the nucleic acid construct of the third aspect and/or herein relevant embodiments thereof.

The term "recombinant host cell" should herein be understood according to the art. As known in the art, recombinant polynucleotide (e.g. DNA) molecules are polynucleotide (e.g. DNA) molecules formed by laboratory methods of genetic recombination (such as molecular cloning) to bring together genetic material from multiple sources, creating sequences that would not otherwise be found in biological organisms. As understood by the skilled person—a recombinant host cell comprises recombinant polynucleotide (e.g. DNA) molecules and a recombinant host cell will therefore not be understood as covering a natural wildtype cell, such as e.g. a natural wildtype *Dactylopius coccus* cell.

Based on e.g. the sequence information disclosed herein—it is routine work for the skilled person to make a relevant recombinant host cell—for instance, based on the prior art the skilled person knows numerous different suitable recombinant host cells that for years have been used as recombinant host cells for e.g. expression of different polypeptides of interest.

The recombinant host cell may be any suitable cell such as any eukaryotic cell [e.g. mammalian cells (such as e.g. Chinese hamster ovary (CHO) cells) or a plant cell] or any prokaryotic cell.

Particularly preferred is wherein the recombinant host cell is a plant cell producing flavokermesic acid/kermesic acid or other related compound such as e.g. rhubarb plant cell.

Preferably the recombinant host cell is a cell selected from the group consisting of a filamentous fungal cell and a microorganism cell.

Filamentous fungi include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

It may be preferred that the filamentous fungal cell is a cell of a species of, but not limited to, *Acremonium, Aspergillus, Fusarium, Humicola, Mucor, Myceliophthora, Neurospora, Penicillium, Thielavia, Tolypocladium,* and *Trichoderma* or a teleomorph or synonym thereof.

A preferred *Aspergillus* cell is *Aspergillus niger* or *Aspergillus oryzae*.

A preferred microorganism cell herein is a microorganism cell selected from the group consisting of a yeast cell and prokaryotic cell.

A preferred yeast cell is a yeast cell selected from the group consisting of Ascomycetes, Basidiomycetes and fungi imperfecti. Preferably a yeast cell selected from the group consisting of Ascomycetes.

Preferred Ascomycetes yeast cell selected from the group consisting of *Ashbya, Botryoascus, Debaryomyces, Hansenula, Kluveromyces, Lipomyces, Saccharomyces* spp e. g. *Saccharomyces cerevisiae, Pichia* spp., *Schizosaccharomyces* spp.

A preferred yeast cell is a yeast cell selected from the group consisting of *Saccharomyces* spp, e. g. *Saccharomyces cerevisiae*, and *Pichia* spp.

A preferred prokaryotic cell is selected from the group consisting of *Bacillus, Streptomyces, Corynebacterium, Pseudomonas*, lactic acid bacteria and an *E. coli* cell.

A preferred *Bacillus* cell is *B. subtilis, B. amyloliquefaciens* or *B. licheniformis*.

A preferred *Streptomyces* cell is *S. setonii* or *S. coelicolor.*

A preferred *Corynebacterium* cell is *C. glutamicum*.

A preferred *Pseudomonas* cell is *P. putida* or *P. fluorescens*.

A Method for Producing Flavokermesic Acid (FK) Glycoside and/or Kemesic Acid (KA)

As discussed above—a sixth aspect of the present invention relates to a method for producing flavokermesic acid (FK) glycoside and/or kermesic acid (KA) glycoside, wherein the method comprises following steps:
(A): contacting in vitro or in vivo in a recombinant host cell comprising a glycosyltransferase gene encoding a glycosyltransferase:
  (a1): flavokermesic acid (FK) with a glycosyltransferase capable of glycosylating the flavokermesic acid under suitable conditions wherein there is produced the flavokermesic acid glycoside; and/or
  (a2): kermesic acid (KA) with a glycosyltransferase capable of glycosylating the kermesic acid under suitable conditions wherein there is produced the kermesic acid glycoside.

It may be preferred that the recombinant host cell in step (A) is a recombinant host cell comprising a recombinant glycosyltransferase gene encoding a glycosyltransferase.

Preferably, the glycosyltransferase in step (a2) is a glucosyltransferase and there thereby in step (a2) is produced kermesic acid glucoside, preferably wherein the produced kermesic acid glucoside is Carminic acid (FIG. 1 herein shows the structure of Carminic acid).

It may be preferred that the glycosyltransferase in step (a1) is a glucosyltransferase and there thereby in step (a1) is produced flavokermesic acid glucoside, preferably wherein the produced flavokermesic acid glucoside is the compound DcII (FIG. 1 herein shows the structure of the compound DcII).

When the produced compound in step (a1) is DcII it may be preferred to use this DcII as an intermediate to make Carminic acid.

This may be done by chemical synthesis and the skilled person knows based on his common general knowledge how to do this.

Alternatively, it may be done enzymatically by e.g. using a suitable oxygenase. An example of a suitable oxygenase is cytochrome P450 superfamily of monooxygenases (officially abbreviated as CYP) enzyme. Other examples are flavine monooxygenases or different types of dioxygenases, this list not to be considered excluding the involvement of other classes of enzymes As known in the art—the most common reaction catalyzed by cytochromes P450 is a monooxygenase reaction, e.g., insertion of one atom of oxygen into a substrate.

As understood by the skilled person in the present context—the terms flavokermesic acid (FK) and/or kermesic acid (KA) aglycons of step (a) of the method of the sixth aspect as discussed herein should be understood as the FK and/or KA specific compounds shown in FIG. 1 and equivalent analogs of these specific compounds with minor substituents (e.g. a FK methyl ester).

As understood in by the skilled person—if FK methyl ester is used as aglycon in step (a) of the method of the sixth aspect then there will via the glycosylation step be generated a FK methyl ester glycoside, which by routine removal of the methyl group will generate DcII—accordingly FK methyl ester aglycon may be seen as equivalent to FK aglycon in relation to the method of the sixth aspect as discussed herein.

In step (a) of the method of the sixth aspect is specified that there is used a glycosyltransferase capable of glycosylating FK and/or KA—accordingly it is understood that the GT must be capable of doing this.

It may be preferred to purify the glycoside produced in step (A)—i.e. in step (a1) and/or in step (a2).

Accordingly it may be preferred that the method of the sixth aspect comprises a further step (B) with following steps:
  (B): purifying the produced glycoside in step (a1) and/or in step (a2) whereby one gets a composition, wherein at least 5% w/w (preferably at least 10% w/w, more preferably at least 50% w/w and most preferably at least 80% w/w) of the compounds in the composition is the produced flavokermesic acid glycoside and/or kermesic acid glycoside.

The skilled person knows how to purify such glycoside compounds and it may be done according to the art.

The purifying step (B) may be particularly preferred when:
  the produced glycoside in step (a2) is Carminic acid;
  the produced glycoside in step (a1) is compound DcII; and/or
  the produced glycoside in step (a1) is compound DcII and it is used as an intermediate to make Carminic acid.

As discussed herein—in working Examples there was made a contacting in vitro of flavokermesic acid (FK) and/or kermesic acid (KA) with the glycosyltransferase of SEQ ID NO:2. It may be seen as routine work for the skilled person to perform such an in vitro contacting step.

The glycosyltransferase of SEQ ID NO:2 was recombinantly expressed in a yeast cell (see working Example herein)—accordingly, in a working Example herein there was made a recombinant yeast host cell comprising a recombinant glycosyltransferase gene encoding a glycosyltransferase of SEQ ID NO:2.

It is believed that if flavokermesic acid (FK) and/or kermesic acid (KA) would be added under suitable condition to a fermentation medium the FK and/or KA compound(s) would enter into e.g. yeast cells fermented in the medium—accordingly, if e.g. the yeast cells are recombinant yeast host cells comprising a recombinant glycosyltransferase gene encoding a glycosyltransferase then there would be made a contacting in vivo in a recombinant host cell of FK and/or KA with a glycosyltransferase.

In a preferred embodiment the contacting in step (A) is in vivo and the recombinant host cell is a yeast cell, preferably wherein the yeast cell is selected from the group consisting of *Saccharomyces* spp (e.g. *Saccharomyces cerevisiae*) and *Pichia* spp.

Above is described preferred recombinant host cells—these preferred recombinant host cells may also be preferred recombinant host cells in relation to the method of the sixth aspect of the present invention.

In the present context—it may be said that it is within the skilled person's common knowledge to identify a suitable recombinant host cell to perform the in vivo contacting step (A) of the method of the sixth aspect and it is not believed that it is necessary to describe this in many details herein.

Above is discussed that preferred recombinant host cells may e.g. be a microorganism cell or a filamentous fungal cell—these cells may be preferred recombinant host cells in relation to the method of the sixth aspect.

It may be possible to make a recombinant host cell (e.g. a recombinant host microorganism cell) which comprises a gene encoding a product involved in the biosynthesis pathway leading to flavokermesic acid (FK) and/or kermesic acid (KA) and such a recombinant host cell could be preferred herein.

Accordingly, it may be preferred that the contacting in step (A) is contacting in vivo in a recombinant host cell comprising a recombinant glycosyltransferase gene encoding a glycosyltransferase and a gene encoding a product involved in the biosynthesis pathway leading to flavokermesic acid (FK) and/or kermesic acid (KA).

As discussed in working Example herein—the GT of SEQ ID NO:2 is membrane bound or hydrophobic/insoluble in vivo and in water. When production cells or fractions of cells containing the membrane bound GT are separated from the product (e.g. carminic acid), the GT can essentially not be present in the fraction where the more soluble product/hydrophilic product is present. This is an advantage for obtaining a final product (e.g. carminic acid product/composition) which is essentially totally free of the recombinant GT.

Because the substrates glycosylated by the GT may be hydrophobic aglycons, the aglycons would be expected to partly accumulate in membranes and other hydrophobic parts of the production cells. By the use of a membrane bound GT a more efficient glycosylation of hydrophobic compounds present in e.g. membranes is obtained Accordingly, in a preferred embodiment the glycosyltransferase used in the method of the sixth aspect is a GT which is membrane bound or insoluble in water.

In a preferred embodiment—the glycosyltransferase in step (A) of the method of the sixth aspect is a glycosyltransferase of the first aspect and/or herein relevant embodiments thereof.

As discussed herein—the identified data/results of working Examples 4 show that herein relevant GT enzymes can be identified in e.g. *Sorghum* and rice plants.

The *Sorghum* polypeptide sequence (Genbank ID number: AAF17077.1) is shown as SEQ ID NO: 4 herein.

The rice polypeptide sequence (Genbank ID number: CAQ77160.1) is shown as SEQ ID NO: 5 herein.

It may be relevant that the glycosyltransferase in step (A) of the method of the sixth aspect is a glycosyltransferase comprising an amino acid sequence which has at least 70% (preferably at least 80%, more preferably at least 90% and even more preferably at least 98%) identity with amino acids 1 to 492 of SEQ ID NO:4.

It may be relevant that the glycosyltransferase in step (A) of the method of the sixth aspect is a glycosyltransferase comprising an amino acid sequence which has at least 70% (preferably at least 80%, more preferably at least 90% and even more preferably at least 98%) identity with amino acids 1 to 471 of SEQ ID NO:5.

EXAMPLES

Example 1—Cloning of *D. Coccus GT* and Test of its FK and KA Activity

Materials and Methods
Purification of DNA and mRNA

Fresh frozen *Dactylopius coccus* (were obtained from Lanzarote). Fresh frozen *Porphyrophora polonica* were obtained from Poland. The frozen insects were ground into powder under liquid nitrogen and DNA/RNA was purified: DNA was purified using DNeasy Blood & Tissue kit (Qiagen), according to the protocol of the supplier. RNA was purified using RNeasy mini kit (Qiagen) according to the protocol of the supplier. Eucaryote mRNA was made into cDNA using RT$^2$ Easy First Strand Kit (Qiagen) according to the protocol of the supplier using poly-dT priming of the revers transcriptase reaction.

Sequencing of DNA and RNA:

DNA and cDNA were sent for sequencing at BGI (Shenzen, China) for sequencing using 100 bp paired-end Illumina technology according to the protocol of Illumina at a coverage of approximately 60-100× and the output in fastq data format.

Analysis of DNA and RNA/cDNA Sequences:

The obtained fastq-sequences of DNA and RNA/cDNA were imported into Genomic Workbench version 5.4 (CLC-bio, Århus, Denmark) and assembled using the de novo assembling algorithm into contigs. Output files were exported as FASTA format. RNA/cDNA FASTA files were then imported into IOGMA v. 10 (Genostar, Grenoble, France) and putitative genes were identified using the "hidden Markov-Matrix-based prokaryote gene-finder.

Putative genes were annotated using BLAST (basic local alignment sequence tool) against genbank (NCBI) using as well the nucleotide sequence as the translated protein sequence. The putative genes were also annotated by similarity comparison to PFAM databases of protein families.

Preparation of Protein Fractions from *D. Coccus*

Three grams of fresh *D. coccus* insects were homogenized in 120 mL of isolation buffer [350 mM sucrose, 20 mM Tricine (pH 7.9), 10 mM NaCl, 5 mM DTT, 1 mM PMSF) containing 0.3 g polyvinylpolypyrrolidone. The homogenate was filtered through a nylon cloth (22 μm mesh) and centrifuged for (10 min, 10,000×g at 4° C.). The supernatant was centrifuged (1 h, 105,000×g, at 4° C.), yielding a soluble and a membrane bound protein fraction. The soluble protein fraction was concentrated to 1 mL and buffer-exchanged with 20 mM Tricine (pH 7.9), 5 mM DTT by using Amicon ultrafugation-3K devices (Millipore). The membrane bound protein pellet was washed 3 times by resuspending the pellet in 60 mL of 20 mM Tricine (pH 7.9), 5 mM DTT using a marten paintbrush followed by re-centrifugation. The membrane bound protein pellet was finally resuspended in 1 mL 20 mM Tricine (pH 7.9), 5 mM DTT. The soluble protein fraction and the membrane bound protein fraction were analyzed for glycosylation activity.

Purification of a Flavokermesic Acid/Kermesic Acid-Specific GT Activity from *D. Coccus* Membrane Proteins A membrane bound protein fraction isolated from 3 g fresh *D. coccus* insects was solubilized by adding 1% (v/v) Triton x-100 (reduced form) and gently stirring for 1.5 h in the cold. The Triton x-100 treated solution was centrifuged (1 h, 105,000×g, at 4° C.) and the supernatant was isolated and applied to a column packed with 2 mL Q-sepharose Fast flow (Pharmacia). The column was washed in 4 mL of buffer A [20 mM Tricine (pH 7.9), 0.1% (v/v) Triton x-100 (reduced form), 50 mM NaCl] and proteins were eluted with 20 mM Tricine (pH 7.9), 0.1% (v/v) Triton x-100 (reduced form)] using a discontinuous NaCl gradient from 100 mM-500 mM, (with 50 mM increments). 0.5-ml-fractions were collected, desalted, analyzed by SDS-PAGE and monitored for glucosylation activity using the described radiolabeled glucosylation enzyme assay. A fraction containing enriched flavokermesic acid/kermesic acid-specific GT activity was subjected to peptide mass fingerprinting analysis.

Enzyme Assays and Glucoside Product Detection

Glucosylation of flavokermesic acid and kermesic acid was performed in assay mixtures of 60 µL containing 20 mM Tricine (pH 7.9), 3.3 µm UDP[14C]glucose and 20 uL protein extract (membrane bound or soluble protein). Reactions were incubated for 0.5 h at 30° C. and terminated by adding 180 µL of methanol. Samples were centrifuged at 16,000×g for 5 min at 4° C. and supernatant was spotted on TLC plates (silica gel 60 F254 plates; Merck). Assay products were resolved in dichloromethane:methanol:formic acid (7:2:2, by volume). Radiolabeled products were visualized using a STORM 840 PhosphorImager (Molecular Dynamics, http://www.moleculardynamics.com).

Expression of Codon Optimized DcUGT2, DcUGT4 and DcUGT5 in *S. cerevisiae*

A synthetic codon optimized version of DcUGT2 and two other putative GT sequences from the *D. coccus* transcriptome termed DcUGT4 and DcUGT5 for yeast expression was purchased from GenScript with flanking gateway recombination attL sites. The synthetic fragments were used as PCR templates with specific primers to generate the corresponding C-terminal StrepII-tagged versions. The six gene constructs (tagged and non-tagged fragments) were cloned into the gateway destination plasmid pYES-DEST52 (Invitrogen) using LR clonasell enzyme mix. The six pYES-DEST52 plasmid constructs were transformed separately into the Invsc1 yeast strain (Invitrogen) and positive transformants were verified by PCR. Heterologous protein production was performed according to the instructions of the pYES-DEST52 gateway vector (Invitrogen). Production of heterologous StrepII-tagged protein was verified by western blotting using anti-Strep antibody. A membrane bound protein fraction was prepared from verified yeast transformants as described in (D. Pompon, B. Louerat, A. Bronine, P. Urban, Yeast expression of animal and plant P450s in optimized redox environments, Methods Enzymol. 272 (1996) 51-64) and screened for glucosylation activity towards flavokermesic acid/kermesic acid. The yeast optimized sequence is shown in SEQ ID NO: 3 herein.

LC-MS-MS

LC/MS was performed on an Agilent Q-TOF with the following HPLC system:

Column Kinetix 2.6µ XB-C18 100A (100×4.60 mm, Phenomenex). Solvent A (900 ml deionized water, 100 ml methanol and 50 ml formic acid). Solvent B (700 ml methanol, 300 ml deionized water and 50 ml formic acid).

Flow 0.8 ml/min. 35° C.

Gradient elution. 0-1 min 100% A. Linear gradient to 83% A 3 min. linear gradient to 63% A 6 min, linear gradient to 45% A 9 min, linear gradient to 27% A 12 min, linear gradient to 10% A 15 min, linear gradient to 3% A 17 min, linear gradient to 2% A 19 min, linear gradient to 0% A 20 min, 0% A 22 min, linear gradient to 100% A 25 min. Retention times were 7.6 min for carminic acid, 7.8 min for DC II, 13.7 min for flavokermesic acid and 13.9 min for kermesic acid.

Results:

The ability to glycosylate flavokermesic acid/kermesic acid using C14-UDP-glucose as a substrate was detected in homogenized *D. coccus* insects. The activity was shown to be membrane bound and the activity was purified and the purified proteins were submitted to proteomics analysis. It was shown that the enzymatic activity was to come from a polypeptide with a sequence corresponding to our candidate gene DcUGT2.

As discussed above—the herein relevant glycosyltransferase enzyme of SEQ ID NO: 2 may herein be termed "DcUGT2".

The amino acid sequence of DcUGT2 shows less than 45% homology to any known glycosyl transferase.

Knowing that cloning the wildtype sequence into yeast had given no relevant enzyme activity, we redesigned the nucleotide sequence of DcUGT2 to a sequence coding for the same polypeptide but using nucleotide codons optimized for *S. cerevisiae*, a process called codon optimization (the *S. cerevisiae* optimized sequence is shown as SEQ ID No. 3 herein). Subsequently the codon optimized sequence of DcUGT2 was cloned and expressed in yeast. The heterologous yeast strain contains a membrane bound enzyme activity capable of glucosylating kermesic acid and flavokermesic acid.

After obtaining peptide mass fingerprinting data from a *D. coccus* protein fraction enriched with GT activity towards flavokermesic acid/kermesic acid, we matched the peptide masses to the transcriptomic dataset and identified three putative UGTs (DcUGT2, DcUGT4 and DcUGT5).

Heterologous expression of the three candidates in yeast revealed that only one of these UGTs, namely DcUGT2 was responsible for the observed glucosylation activity towards flavokermesic acid/kermesic acid in the *D. coccus* protein fraction.

A viscozyme treatment of the generated C-14 radiolabelled glucoside, showed that it was resistant towards hydrolysis, further suggesting that the DcUGT2 is a C-GT, responsible for producing DCII and carminic acid.

A LC-MS-MS showed formation of products with the same retention time, spectrum, molecular mass and molecular degradation pattern as DcII and carminic acid respectively.

Conclusion

The result of this example 1 demonstrated that it was not an easy task to isolate/clone the herein relevant glycosyltransferase enzyme of SEQ ID NO: 2, which may herein be termed "DcUGT2".

For instance, the identified gene sequences of the genome and transcriptome of *D. coccus* insects were analyzed for similarity to herein relevant public known C-glycosyltransferase sequences and the result was negative in the sense that none of the identified gene sequences of the genome/transcriptome showed herein significant similarity to publicly known herein relevant C-glycosyltransferase sequences.

However, even though the bioinformatic sequence similarity analysis could be said to indicate that the genome of *Dactylopius coccus* would not comprise a gene encoding a herein relevant glycosyltransferase—the present inventors continued to investigate the matter and the present inventors identified a *Dactylopius coccus* extract (including extracts of the endosymbionts present in *D. coccus*) with herein relevant GT activity and by a combination of herein relevant purification and testing steps the inventors were finally able to get a relatively pure fraction/composition wherefrom it was possible to obtain several partial amino acid sequences of possible GT enzyme candidates.

The present inventors tested the activity of the herein described isolated/cloned novel glycosyltransferase of SEQ ID NO: 2 (DcUGT2) and found that it was able to conjugate glucose to the aglycons flavokermesic acid (FK) and kermesic acid (KA)—see FIG. 1 herein.

Example 2 Testing KA GT Activity of Prior Art Known UrdGT2

As discussed above—the UrdGT2 is described in the article Baig et al (Angew Chem Int Ed Engl. 2006 Nov. 27; 45(46):7842-6).

As discussed above—this article describes that UrdGT2 is capable of glycosylating different aglycon molecules that may be considered structurally similar to the herein relevant Kermesic acid (KA) and Flavokermesic acid (FK) aglycons.

A codon optimized synthetic version of UrdGT2 for *E. coli* expression was cloned and recombinantly expressed in *E. coli*. A crude soluble protein extract containing the the recombinant UrdGT2 was obtained—i.e. an extract comprising the UrdGT2

The UrdGT2 GT activity was analyzed in vitro using either UDP-glucose or TDP-glucose as a sugar donor and FA/KA as aglycone substrates. No activity was detected towards these aglycons—i.e. no herein relevant GT activity was identified in relation to these aglycons.

However, it was confirmed that the recombinant UrdGT2 was active, as demonstrated by the in vitro formation of a C14-radiolabelled glucoside derived from the glucosylation of an unidentified compound in the crude *E. coli* extract.

Example 3 GT Activity in Aloe Plant and *Haworthia* Plant

Isolation and Test of GT Activity from Aloe
1) The plant was washed from soil particles and separated into: A) Root, B) Green leaf tissue and C) the gel material from the leaf
2) 5 g of tissue was frozen immediately in liquid nitrogen and ground in a cold mortar with a pestle to a fine powder.
3) 20 mL of cold extraction buffer [20 mM Tricine-HCl, 10 mM NaCl, 5 mM DTT, 1 mM PMSF, pH 7.9] containing a Complete protease inhibitor without EDTA (Roche), 0.1% (w/v) proteamine sulfate and 0.5 g of PVPP were added to the powder and vortexed.
4) The homogenate was gently stirred at 4° C. for 10 min and then centrifuged at 12,000×g at 4° C. for 5 min.
5) Supernatant was isolated and 1 mL of 2% (w/v) proteamine sulfate in 20 mM Tricine-HCl, pH 7.9 was added dropwise over 2 min at 4° C. under constant stirring.
6) The supernatant was filtered through 2 pieces of nylon mesh. The filtered supernatant was then centrifuged at 12,000 xg at 4° C. for 5 min.
7) The supernatant was isolated and ultracentrifuged at 110,000×g at 4° C. for 1 h.
8) The soluble protein fraction (supernatant) was isolated and buffer-exchanged 5 times with 20 mM Tricine-HCl, pH 7.9 containing 5 mM DTT using a Amicon Ultra centrifugal filter device-3K (Millipore)
9) 20 µL soluble protein extract was incubated in a total reaction volume of 60 µL containing UDP-glucose (1.25 mM final conc.) and either FK (50 µM final conc.), KA (50 µM final conc) or MeO-FK/EtO-FK (50 µM/50 µM final conc) for 2 h at 30° C., shaking at 650 rpm.
10) Enzyme reactions were terminated with 180 µL cold methanol and filtered through a 0.45 micron filter and subjected to HPLC-MS analysis.

TABLE 1

Glucosides formed in in vitro glucosylation assays using enzyme extracts from *Aloe*.

| | m/z [M − H]⁻ values | | | |
|---|---|---|---|---|
| *Aloe* Soluble protein | 475 m/z [M − H]⁻ FK-monoglc | 491 m/z [M − H]⁻ KA-monoglc | 489 m/z [M − H]⁻ MeOFK-monoglc | 503 m/z [M − H]⁻ EtOFK-monoglc |
| Leaf | 3.73 | 3.71 | 5.81 | 6.63 |
| Gel | | | | |
| Root | | 3.71 | | |

Crude soluble enzyme extracts of three Aloe tissues, green leaf material (Leaf), gel material from the leaf (Gel) and Root were tested for glucosylation activity towards flavokermesic acid (FK), kermesic acid (KA), methyl ester of flavokermesic acid (MeOFK) and ethyl ester of flavokermesic acid (EtOFK). Numbers correspond to retention times (min) after HPLC-MS separation of the novel glucosides formed in vitro (Table 1).

The m/z values 475 and 491 are the same m/z values as are obtained for DcII and CA, respectively, solubilized in similar solutions. Both m/z values are 162 (m/z value of glucose in a glucoside) higher than the m/z values of the FK and KA indicating that the glucose moiety from UDP-glucose in the reaction buffer has been transferred to the aglycone by a GT in the extract. The m/z [M-H] values 489 and 503 are also 162 higher than the m/z values obtained with MeOFK and EtOFK, respectively, indicating that a glucose unit has been added to both MeOFK and EtOFK by a GT present in the extract.

Isolation and Test of GT Activity from *Haworthia limifolia*

The procedure was as described for Aloe but plant tissue analyzed were following: A) Green leaf tissue, B) Gel material from the leaf, C) Base tissue (pink part between root and stem) and D) Root tissue.

Crude soluble enzyme extracts of four *Haworthia limifolia* tissues, green leaf material (Leaf), gel material from the leaf (Gel), pink tissue between root and stem (Base) and Root were tested for glucosylation activity towards flavokermesic acid (FK), kermesic acid (KA), methyl ester of flavokermesic acid (MeOFK) and ethyl ester of flavokermesic acid (EtOFK). Numbers correspond to retention times (min) after HPLC-MS separation of the novel glucosides formed in vitro (Table 2).

TABLE 2

Glucosides formed in in vitro glucosylation assays using enzyme extracts from *Haworthia limifolia*.

| | m/z [M − H]⁻ values | | | |
|---|---|---|---|---|
| Haworthia Soluble protein | 475 m/z [M − H]⁻ FK-monoglc | 491 m/z [M − H]⁻ KA-monoglc | 489 m/z [M − H]⁻ MeOFK-monoglc | 503 m/z [M − H]⁻ EtOFK-monoglc |
| Leaf Gel | 3.73 | 3.71 | 5.81 | 6.63 |
| Base | 3.73 | 3.71 | 5.81 | 6.63 |
| Root | 3.73 | 3.71 | 5.81 | 6.63 |

The m/z values 475 and 491 are the same m/z values as are obtained for DcII and CA, respectively, solubilized in similar solutions. Both m/z values are 162 (m/z value of glucose in a glucoside) higher than the m/z values of the FK and KA indicating that the glucose moiety from UDP-glucose in the reaction buffer has been transferred to the aglycone by a GT in the extract. The m/z [M-H] values 489 and 503 are also 162 higher than the m/z values obtained with MeOFK and EtOFK, respectively, indicating that a glucose unit has been added to both MeOFK and EtOFK by a GT present in the extract.

Conclusion

The results of this example demonstrate that herein relevant glycosyltransferase (GT) enzymes can be identified in Aloe plants and *Haworthia* plants.

Said in other words, Aloe plants and *Haworthia* plants comprise a glycosyltransferase which is capable of glycosylating flavokermesic acid in order to produce flavokermesic acid glycoside; and/or capable of glycosylating kermesic acid in order to produce kermesic acid glycoside.

Example 4 GT Activity in *Sorghum* and Rice Plant

As known the art—*Sorghum* and rice plants comprise glycosyltransferases.

As known in the art—some of the *Sorghum* and rice glycosyltransferases may glycosylate low molecular weight aglycone compounds.

The in the art described glycosyltransferases from *Sorghum* and rice plants have significant less than 70% identity with amino acids 1 to 515 of SEQ ID NO:2 as disclosed herein.

It is not known in the art if glycosyltransferases of *Sorghum* and/or rice plants would be a herein relevant glycosyltransferase—i.e. a glycosyltransferase which is capable of glycosylating flavokermesic acid in order to produce flavokermesic acid glycosides; and/or capable of glycosylating kermesic acid in order to produce kermesic acid glycosides.

The known glycosyltransferases from *Sorghum* (*Sorghum bicolor*), SbUGT85B1, with Genbank ID number AF199453.1 (nucleotide seq.)/AAF17077.1 (polypeptide seq) and rice (*Oryza sativa*), OsCGT, with Genbank ID number FM179712.1 (nucleotide seq.)/CAQ77160.1 (polypeptide seq) were expressed in *E. coli* strain Xjb and crude *E. coli* proteins extracts were prepared and tested for glucosylation activity on the substrates kermesic acid and flavokermisic acid as described by Kannangara et al. (2011) and Augustin et al. (2012).

FIG. 2A shows LC-MS analyses of glucosylated products formed in assays containing crude lysate of *E. coli* strain Xjb expressing either SbUGT85B1 or OsCGT, UDP-glucose and flavokermesicc acid (FK) or kermesic acid (KA). As a negative control crude extract from the *E. coli* strain Xjb was used in the assays.

There were identified KA glycosides (491 m/z [M-H]— the m/z[M-H] value of CA) for both glycosyltransferases and FK glycosides (475 m/z [M-H] the m/z[M-H] value of DcII) for OsCGT.

Conclusion

The result of this example demonstrated that herein relevant glycosyltransferase (GT) enzymes can be identified in *Sorghum* and/or rice plants.

Said in other words, *Sorghum* and/or rice plants comprise a glycosyltransferase which is capable of glycosylating flavokermesic acid in order to produce flavokermesic acid glycoside; and/or capable of glycosylating kermesic acid in order to produce kermesic acid glycoside.

Example 5 Use of Endogenous GT Gene or GT Activity

As known in the art glycosyltransferases able to glycosylate low molecular weight are present in a lot of different organisms. A method to contact the glycosyltransferase of the cells of an organism with a low molecular weight compound is to introduce one or more genes directing the biosynthesis of the low molecular weight compound and thus enabling the cells to glycosylate the low molecular weight compound. The low molecular weight compound may be e.g. flavokermesic acid or kermersic acid or decorated versions of these molecules.

One or more genes directing the biosynthesis of flavokermesic acid or kermesic acid or decorated version of these molecules are introduced into a glycosyltransferase containing organism, e.g. the tobacco plant, *Nicotiana benthamiana*.

When the gene/genes is/are transiently expressed according to the methods described in D'Aoust et al. (2008) in e.g. plant tissue the low molecular weight compound or compounds is/are produced. Cells stably expressing the gene/genes are produced and selected according to the methods described in Gelvin (2003).

In cells containing either stably expressed and/or transiently expressed gene/genes the low molecular weight compounds come into contact with the endogenous glycosyltransferases, resulting in the formation of one or more glycosides of flavokermesic acid, kermesic acid or decorated versions of these molecules.

The presence of the glycosides is demonstrated by the extraction and the analytical methods described in example 3.

Samples are prepared for LC/MS by the method for extraction described by Rauwald and Sigler (1994).

Conclusion

The results of this example demonstrate that endogenous glycosyltransferases present in the cells of a recombinant organism can be used to convert flavokermesic acid, kermesic acid or decorated versions of these molecules into glycosides when a gene/genes directing the biosynthesis of the aglycons are introduced into the organism.

Said in other words introduction of a gene or genes directing the biosynthesis of flavokermesic acid, kermesic acid, decorated versions of these molecules, or related low molecular weight compounds is a method to bring the low molecular weight compound in contact with glycosyltransferases and thus a method to produced glycosides of flavokermesic acid, kermesic acid or decorated version of these compounds.

REFERENCES

1: U.S. Pat. No. 5,424,421 (European Colour, published 1995)
2: WO2006/056585A1 (Chr. Hansen A/S)
3: Stathopoulou et al (Analytica Chimica Acta 804 (2013) 264-272)
4: Zagrobelny et al (Cyanogenic glucosides and plant-insect interactions; Phytochemistry. 2004 February; 65(3):293-306)
5: Geuder et al (Journal of Chemical Ecology, Vol. 23, No. 5, 1997)
6: Genta et al, (Potential role for gut microbiota in cell wall digestion and glucoside detoxification in *Tenebrio molitor* larvae), Journal of Insect Physiology 52 (2006) 593-601
7: WO2004/111254A1 (Poalis A/S)
8: Gutmann et al (Pure Appl. Chem, 2013-07-09)
9: Pompon et al (Methods Enzymol. 272 (1996):51-64)
10: Baig et al (Angew Chem Int Ed Engl. 2006 Nov. 27; 45(46):7842-6)
11: Radominska-Pandya A, Bratton S M, Redinbo M R, Miley M J. Drug Metab Rev. 2010 February; 42(1):133-44)
12: Plant Physiology, November 2008, Vol. 148, pp. 1295-1308
13: Esben Halkjaer Hansen et al. Phytochemistry 70(4): 473-482
14: Kannangara et al. (Plant Journal. 68 (2011): 287-301)
15: Augustin et al. (Plant Physiology. 160 (2012): 1881-1895)
16: D'Aoust et al. (Methods Mol Biol 483 (2009): 41-50)
17: Gelvin (Microbiol Mol Biol Rev 67(1) (2003): 16-37)
18: Rauwald and Sigler (Phytochemical Analysis 5 (1994): 266-270)

We claim:

1. A method for producing flavokermesic acid glycoside or kermesic acid glycoside comprising the acts of:
providing an aglycon wherein said aglycon comprises flavokermesic acid or kermesic acid;
providing a sugar, wherein said sugar comprises a nucleotide activated glucose;
providing a recombinant cell wherein said recombinant cell comprises an expression cassette comprising an isolated polynucleotide comprising a nucleotide sequence which encodes an isolated glycosyltransferase polypeptide capable of:
(I): conjugating nucleotide activated glucose to flavokermesic acid (FK); and/or
(II): conjugating nucleotide activated glucose to kermesic acid (KA);
and wherein the glycosyltransferase polypeptide is at least one polypeptide selected from the group consisting of:
(a) a polypeptide comprising an amino acid sequence which has at least 95% identity with amino acids 1 to 515 of SEQ ID NO:2; and (b) a polypeptide comprising an amino acid sequence which has at least 95% identity with amino acids 20 to 468 of SEQ ID NO:2; and wherein said polynucleotide is operably linked to one or more control sequences that direct the production of the polypeptide in an expression host; and contacting said glycosyltransferase polypeptide with said aglycon and said nucleotide activated glucose to produce flavorkermesic acid glycoside or kermesic acid glycoside.

2. The method of claim 1, wherein said cell is *Saccharomyces* spp. or *Pichia* spp.

3. The method of claim 2, wherein said cell is *Saccharomyces cerevisiae*.

4. The method of claim 1, wherein said nucleotide activated glucose comprises UDP-glucose.

5. The method of claim 1, wherein said expression cassette comprises a plasmid.

6. The method of claim 1, further comprising the act of purifying said produced flavokermesic acid glycoside or kermesic acid glycoside.

7. A method for producing flavokermesic acid glycoside or kermesic acid glycoside in vitro comprising the acts of:

providing an aglycon wherein said aglycon comprises flavokermesic acid or kermesic acid;

providing a sugar, wherein said sugar comprises a nucleotide activated glucose;

providing an isolated recombinant glycosyltransferase produced by recombinant cell wherein said recombinant cell comprises an expression cassette comprising an isolated polynucleotide comprising a nucleotide sequence which encodes an isolated glycosyltransferase polypeptide capable of:

(I): conjugating nucleotide activated glucose to flavokermesic acid (FK); and/or (II): conjugating nucleotide activated glucose to kermesic acid (KA);

and wherein the glycosyltransferase polypeptide is at least one polypeptide selected from the group consisting of:

(a) a polypeptide comprising an amino acid sequence which has at least 95% identity with amino acids 1 to 515 of SEQ ID NO:2; and (b) a polypeptide comprising an amino acid sequence which has at least 95% identity with amino acids 20 to 468 of SEQ ID NO:2; and wherein said polynucleotide is operably linked to one or more control sequences that direct the production of the polypeptide in an expression host; and contacting said glycosyltransferase polypeptide with said aglycon and said nucleotide activated glucose to produce flavokermesic acid glycoside or kermesic acid glycoside.

8. The method of claim 7, wherein said cell is *Saccharomyces* spp. or *Pichia* spp.

9. The method of claim 8, wherein said cell is *Saccharomyces cerevisiae*.

10. The method of claim 7, wherein said nucleotide activated glucose comprises UDP-glucose.

11. The method of claim 7, wherein said isolated recombinant glycosyltransferase is isolated by the act of extraction from said recombinant cell comprising a expression cassette which encodes for a glycosyltransferase.

* * * * *